(12) United States Patent
McLendon et al.

(10) Patent No.: US 7,718,600 B2
(45) Date of Patent: May 18, 2010

(54) IAP BINDING COMPOUNDS

(75) Inventors: George McLendon, Durham, NC (US); Rachael A. Kipp, Bridgewater, MA (US); Martin Case, Essex Junction, VT (US); Yigong Shi, Plainsboro, NJ (US); Martin F. Semmelhack, Princeton, NJ (US); Philip A. Albiniak, Muncie, IN (US); Aislyn D. Wist, West Orange, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 642 days.

(21) Appl. No.: 10/521,723

(22) PCT Filed: Jul. 15, 2003

(86) PCT No.: PCT/US03/22071

§ 371 (c)(1),
(2), (4) Date: Apr. 10, 2006

(87) PCT Pub. No.: WO2004/007529

PCT Pub. Date: Jan. 22, 2004

(65) Prior Publication Data

US 2007/0032437 A1 Feb. 8, 2007

Related U.S. Application Data

(63) Continuation-in-part of application No. PCT/US02/17342, filed on May 31, 2002, and a continuation-in-part of application No. 09/965,967, filed on Sep. 28, 2001, now Pat. No. 6,992,063.

(60) Provisional application No. 60/395,918, filed on Jul. 15, 2002, provisional application No. 60/294,682, filed on May 31, 2001, provisional application No. 60/345,630, filed on Jan. 3, 2002, provisional application No. 60/256,830, filed on Dec. 20, 2000, provisional application No. 60/236,574, filed on Sep. 29, 2000.

(51) Int. Cl.
*C07K 4/00* (2006.01)
*C07K 5/00* (2006.01)
(52) U.S. Cl. .......................... 514/2; 514/19
(58) Field of Classification Search ............. None
See application file for complete search history.

(56) References Cited

U.S. PATENT DOCUMENTS

| 5,378,803 A | 1/1995 | Morgan et al. |
| 5,463,124 A | 10/1995 | Jacobi et al. |

FOREIGN PATENT DOCUMENTS

| WO | WO 93/23424 A1 | 11/1993 |
| WO | WO98/16240 | * 4/1998 |
| WO | WO 02/26775 A2 | 4/2002 |
| WO | WO 2004/007529 A2 | 1/2004 |
| WO | WO 2004/066958 A2 | 8/2004 |
| WO | WO 2004/072105 A2 | 8/2004 |

OTHER PUBLICATIONS

Sierra and de la Torre, Angewandte Chemie, 2000, vol. 39, pp. 1538-1559.*
Lin et al, Journal of Biological chemistry, 1995, vol. 270, pp. 14255-14258.*
Ashhab et al., Two splicing variants of a new inhibitor of apoptosis gene with different biological properties and tissue distribution pattern, Mar. 2001, FEBS Letters 495: 56-60.
Deveraux et al., IAP family proteins-suppressors of apoptosis, 1999, Genes & Dev. 13: 239-252.
Kasof et al., Livin, a Novel Inhibitor of Apoptosis Protein Family Member, 2001, J. Biol Chem 276: 3238-3246.
Vucic et al., ML-IAP, a novel inhibitor of apoptosis that is preferentially expressed in human melanomas, 2000, Curr. Biol. 10: 1359-1366.
Du et al., Smac, a Mitochondrial Protein that Promotes Cytochrome c-Dependent Caspase Activation by Eliminating IAP Inhibition, 2000, Cell 102: 33-42.
Verhagen et al., Identification of DIABLO, a Mammalian Protein that Promotes Apoptosis by Binding to and Antagonizing IAP Proteins, 2000, Cell 102:43-53.
Hay, Understanding IAP function and regulation: a view from *Drosophila*, 2000, Cell Death and Diff. 7: 1045-1056.
Greene et al., Protective Groups in Organic Synthesis, 1999, Wiley-Interscience 3$^{rd}$ Edition(TOC only).
Kipp et al. "Molecular Targeting of Inhibitor of Apoptosis Proteins Based on Small Molecule Mimics of Natural Binding Partners" Biochemistry, Jun. 11, 2002, American Chemical Society, vol. 41, pp. 7344-7349.

* cited by examiner

*Primary Examiner*—Karen A Canella
(74) *Attorney, Agent, or Firm*—Pepper Hamilton LLP

(57) ABSTRACT

Compounds that bind cellular IAPs (inhibitor of apoptosis proteins) are disclosed. The compounds are mimetics of the N-terminal tetrapeptide of IAP-binding proteins, such as Smac/DIABOLO, IIid, Grim and Reaper, which interact with a specific surface groove of IAP. Also disclosed are methods of using these compounds for therapeutic, diagnostic and assay purposes.

10 Claims, No Drawings

US 7,718,600 B2

IAP BINDING COMPOUNDS

This application is a CIP of PCT/US03/22071, filed Jul. 15, 2003 which claims benefit of 60/395,918, filed Jul. 15, 2002, the entirety of which is incorporated by reference herein.

This application is a CIP of PCT/US02/17342, filed May 31, 2002, which claims benefit of 60/294,682, filed May 31, 2001 and 60/345,630, filed Jan. 3, 2002. This application is a CIP of 09/965,967, filed Sep. 28, 2001, which claims benefit of 60/236,574, filed Sep. 29, 2000, and 60/256,830, filed Dec. 20, 2000. The entire contents of each of the aforementioned applications are incorporated by reference herein.

Pursuant to 35 U.S.C. §202(c), it is acknowledged that the U.S. Government has certain rights in the invention described herein, which was made in part with funds from the National Institutes of Health, Grant No. GM59348-02.

FIELD OF THE INVENTION

The present invention relates to the field of drug design and development for diagnosis, prevention and treatment of cell proliferative disease. Specifically, the invention features peptidomimetics of the N-terminal tetrapeptide of the mitochondrial protein Smac/DIABOLO (hereinafter Smac), which promotes apotosis in cells through a pathway involving the Inhibitor of Apoptosis Proteins (IAPs), exemplified by XIAP. These peptidomimetics bind IAPs and offer improved pharmacological features as compared with the tetrapeptide.

BACKGROUND OF THE INVENTION

Various scientific articles, patents and other publications are referred to throughout the specification. Each of these publications is incorporated by reference herein in its entirety.

Apoptosis (programmed cell death) plays a central role in the development and homeostasis of all multi-cellular organisms. Alterations in apoptotic pathways have been implicated in many types of human pathologies, including developmental disorders, cancer, autoimmune diseases, as well as neurodegenerative disorders.

Thus, the programmed cell death pathways have become attractive targets for development of therapeutic agents. In particular, since it is conceptually easier to kill than to sustain cells, attention has been focused on anti-cancer therapies using pro-apoptotic agents such as conventional radiation and chemo-therapy. These treatments are generally believed to trigger activation of the mitochondria-mediated apoptotic pathways. However, these therapies lack molecular specificity, and more specific molecular targets are needed.

Apoptosis is executed primarily by activated caspases, a family of cysteine proteases with aspartate specificity in their substrates. Caspases are produced in cells as catalytically inactive zymogens and must be proteolytically processed to become active proteases during apoptosis. In normal surviving cells that have not received an apoptotic stimulus, most caspases remain inactive. Even if some caspases are aberrantly activated, their proteolytic activity can be fully inhibited by a family of evolutionarily conserved proteins called IAPs (inhibitors of apoptosis proteins) (Deveraux & Reed, Genes Dev. 13: 239-252, 1999). Each of the IAPs contains 1-3 copies of the so-called BIR (baculoviral IAP repeat) domain and directly interacts with and inhibits the enzymatic activity of mature caspases. Several distinct mammalian IAPs including XIAP, survivin, and Livin/ML-IAP (Kasof & Gomes, J. Biol. Chem. 276: 3238-3246, 2001; Vucic et al. Curr. Biol. 10:1359-1366, 2000; Ashhab et al. FEBS Lett. 495: 56-60, 2001), have been identified, and they all exhibit anti-apoptotic activity in cell culture (Deveraux & Reed, 1999, supra). As IAPs are expressed in most cancer cells, they may directly contribute to tumor progression and subsequent resistance to drug treatment.

In normal cells signaled to undergo apoptosis, however, the IAP-mediated inhibitory effect must be removed, a process at least in part performed by a mitochondrial protein named Smac (second mitochondria-derived activator of caspases; Du et al. Cell 102: 33-42, 2000) or DIABOLO (direct LIP binding protein with low pI; Verhagen et al. Cell 102: 43-53, 2000). Smac, synthesized in the cytoplasm, is targeted to the inter-membrane space of mitochondria. Upon apoptotic stimuli, Smac is released from mitochondria back into the cytosol, together with cytochrome c. Whereas cytochrome c induces multimerization of Apaf-1 to activate procaspase-9 and -3, Smac eliminates the inhibitory effect of multiple LPs. Smac interacts with all IAPs that have been examined to date, including XLIP, c-IAP1, c-IAP2, and survivin (Du et al., 2000, supra; Verhagen et al., 2000, supra). Thus, Smac appears to be a master regulator of apoptosis in mammals.

Smac is synthesized as a precursor molecule of 239 amino acids; the N-terminal 55 residues serve as the mitochondria targeting sequence that is removed after import (Du et al., 2000, supra). The mature form of Smac contains 184 amino acids and behaves as an oligomer in solution (Du et al., 2000, supra). Smac and various fragments thereof have been proposed for use as targets for identification of therapeutic agents. U.S. Pat. No. 6,110,691 to Wang et al. describes the Smac polypeptide and fragments ranging from at least 8 amino acid residues in length. However, the patent neither discloses nor teaches a structural basis for choosing a particular peptide fragment of Smac for use as a therapeutic agent or target.

Similar to mammals, flies contain two IAPs, DIAP1 and DIAP2, that bind and inactivate several *Drosophila* caspases (Hay, Cell Death Differ. 7: 1045-1056, 2000). DIAP1 contains two BIR domains; the second BIR domain (BIR2) is necessary and sufficient to block cell death in many contexts. In *Drosophila* cells, the anti-death function of DIAP1 is removed by three pro-apoptotic proteins, Hid, Grim, and Reaper, which physically interact with the BIR2 domain of DIAP1 and remove its inhibitory effect on caspases. Thus Hid, Grim, and Reaper represent the functional homologs of the mammalian protein Smac. However, except for their N-terminal 10 residues, Hid, Grim, and Reaper share no sequence homology with one another, and there is no apparent homology between the three *Drosophila* proteins and Smac.

In commonly-owned co-pending U.S. application Ser. No. 09/965,967, it is disclosed that the above described biological activity of Smac is related to binding of its N-terminal four residues to a featured surface groove in a portion of XIAP referred to as the BIR3 domain. This binding prevents XIAP from exerting its apoptosis-suppressing function in the cell. It was further disclosed that N-terminal tetrapeptides from IAP binding proteins of the *Drosophila* pro-apoptotic proteins Hid, Grim and Veto function in the same manner.

Commonly-owned co-pending International Application No. PCT/US02/17342 describes assays for use in high throughput screening or rational drug design of agents that can, like the Smac tetrapeptide or its homologs in other species, bind to a BIR domain of an IAP, thereby relieving IAP-mediated suppression of apoptosis. Those assays are based on competitive displacement of a labeled IAP-binding tetrapeptide by a test compound. That application also describes a library of peptides and N-methyl peptide analogs that were demonstrated by the assay method to bind to the BIR3 domain of XIAP.

The use of peptides for in vivo administration as diagnostic or therapeutic agents is associated with certain disadvantages. These include short half-life due to proteolytic degradation in the body, low absorption through intestinal walls and potential immunogenic reactions, as well as expense involved in peptide synthesis. For these reasons, many current efforts in drug development focus on non-peptidic mimetics that mimic the structure and biological activity of bioactive peptides, but possess improved pharmacologic properties and are easier or less expensive to synthesize.

In connection with the Smac tetrapeptides and homologs described above, then, it would be a significant advance in the art to develop partial peptide or non-peptide mimetics of those molecules. Such mimetics should possess the IAP-binding and apoptosis-promoting bioactivity of the Smac peptides, while also having the improved properties associated with non-peptide mimetics, for use as diagnostic and therapeutic agents in the treatment of cancer.

SUMMARY OF THE INVENTION

The present invention is generally directed to oligopeptides and peptidomimetics, pharmaceutical compositions containing these compounds, and methods for their use as therapeutic and diagnostic agents. The compounds featured herein are mimetics of the N-terminal tetrapeptide of IAP (inhibitor of apoptosis protein)-binding proteins, such as the mammalian Smac/DIABOLO and its homologs, hid, grim and reaper.

In one embodiment, the invention is directed to compounds of formula I:

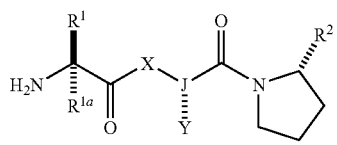

wherein:
R$^1$ is methyl, ethyl, n-propyl, isopropyl, or ethenyl;
R$^{1a}$ is H or methyl;
X is —O—, —S—, —CH$_2$—, or —NH—, and J is —CH— or —N—, provided that when J is —N—, X is —CH$_2$— or —NH—;
Y is H, methyl, ethyl, n-propyl, or isopropyl;
R$^2$ is:

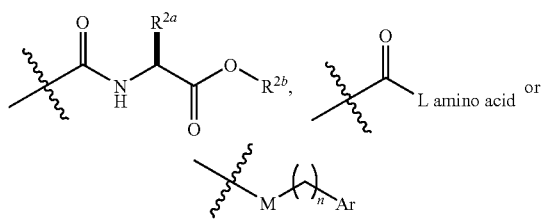

R$^{2a}$ is aryl, cycloalkyl, optionally substituted aralkyl, or cycloalkylalkyl;
R$^{2b}$ is H or alkyl;

M is:

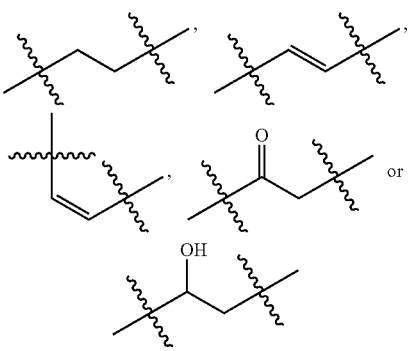

Ar is:

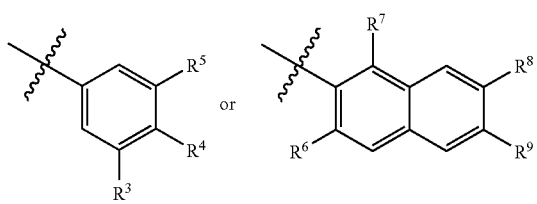

R$^3$, R$^4$, R$^5$, R$^6$, R$^7$, R$^8$, and R$^9$ are each independently H, methyl, ethyl, n-propyl, isopropyl, halo, cyano, —(CH$_2$)$_p$—C(=O)OH, —(CH$_2$)$_p$—C(=O)O-alkyl, —(CH$_2$)$_p$—C(=O)NH$_2$;
n and p are each independently the integer 0, 1, 2, or 3, and the sum of (n+p) is the integer 2 or 3;
provided that at least one of R$^3$, R$^4$, and R5, or at least two of R$^6$, R$^7$, R$^8$, and R$^9$ are each independently H, methyl, ethyl, n-propyl, isopropyl, halo, or cyano;
provided that when one or more of R$^3$ and R$^5$ is isopropyl, R$^4$ is other than isopropyl;
provided that when R$^4$ is isopropyl, R$^3$ and R$^5$ are each independently other than isopropyl;
provided that when R$^8$ is isopropyl, R$^9$ is other than isopropyl; and
provided that when R$^{1a}$ is H, X is —NH—, J is —CH—, Y is H, methyl or isopropyl, and R$^2$ is:

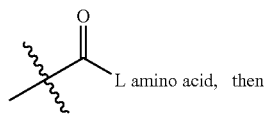

R$^1$ is ethenyl;
or a pharmaceutically acceptable salt thereof.

In another embodiment, the invention is directed to compounds of formula IIa or IIb:

-continued

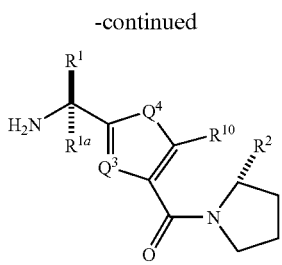

IIb wherein:
R¹ is methyl, ethyl, n-propyl, isopropyl, or ethenyl;
R$^{1a}$ is H or methyl;
Q¹ and Q³ are each independently —O—, —S—, or —NH—;
Q² is —CH—, or —N—;
Q⁴ is —N—;
R² is:

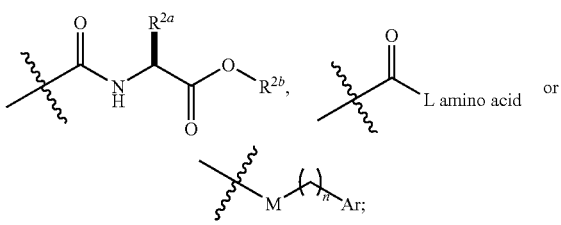

R$^{2a}$ is aryl, cycloalkyl, optionally substituted aralkyl, or cycloalkylalkyl;
R$^{2b}$ is H or alkyl;
M is:

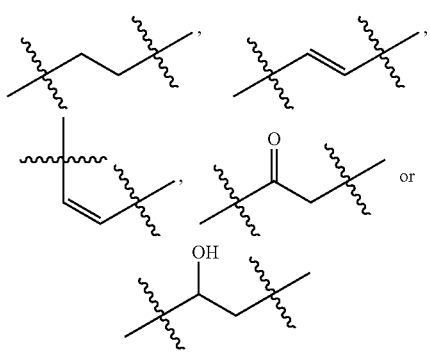

Ar is:

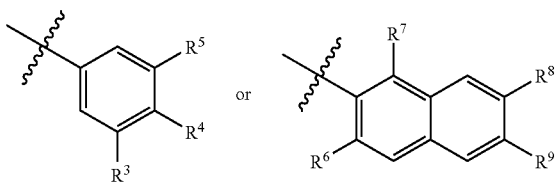

R³, R⁴, R⁵, R⁶, R⁷, R⁸, and R⁹ are each independently H, methyl, ethyl, n-propyl, isopropyl, halo, cyano, —(CH$_2$)$_p$—C(=O)OH, —(CH$_2$)$_p$—C(=O)O-alkyl, —(CH$_2$)$_p$—C(=O)NH$_2$;

R¹⁰ is H or methyl;

n and p are each independently the integer 0, 1, 2, or 3, and the sum of (n+p) is the integer 2 or 3;

provided that at least one of R³, R⁴, and R5, or at least two of R⁶, R⁷, R⁸, and R⁹ are each independently H, methyl, ethyl, n-propyl, isopropyl, halo, or cyano;

provided that when one or more of R³ and R⁵ is isopropyl, R⁴ is other than isopropyl;

provided that when R⁴ is isopropyl, R³ and R⁵ are each independently other than isopropyl;

provided that when R⁸ is isopropyl, R⁹ is other than isopropyl;

or a pharmaceutically acceptable salt thereof.

The foregoing compounds may be formulated as pharmaceutical compositions or as diagnostic agents, or both. As described in greater detail herein, these pharmaceutical compositions and diagnostic agents are used for treatment or detection of cell proliferative disorders, as well as in screening assays for the discovery and development of additional diagnostic and therapeutic agents.

Other features and advantages of the invention will be understood by reference to the detailed description and examples that follow.

DETAILED DESCRIPTION OF ILLUSTRATIVE EMBODIMENTS

As employed above and throughout the disclosure, the following terms, unless otherwise indicated, shall be understood to have the following meanings.

The terms "pharmaceutically active" and "biologically active" refer to the ability of the compounds of the invention to bind IAP (inhibitor of apoptosis protein), specifically the BIR binding groove of IAP, more specifically the BIR3 binding groove of IAP. This biological activity may be measured with respect to any IAP, with XIAP being particularly suitable, and a peptide fragment comprising the BIR3 binding domain of XIAP being an exemplary embodiment.

The pharmaceutically active compounds of the invention are sometimes referred to herein as drugs, to highlight their therapeutic utility in promoting apoptosis by binding IAPs. However, another embodiment of the invention utilizes the compounds as diagnostic agents, for detection of IAP in vitro, in situ or in vivo, or for IAP binding assays. In this embodiment, the compounds of the invention are detectably labeled, for example, with a fluorophore as described in commonly-owned co-pending International Application No. PCT/US02/17342. Another embodiment of the invention utilizes the compounds as targeting agents, i.e., by incorporating into their structure tumor cell-killing or other anti-tumor or therapeutic agents, such as radionuclides. Accordingly, the term "drug" as used herein is intended to refer to all pharmaceutically/biologically active (i.e., IAP-binding) compounds of the invention, for use as therapeutic or diagnostic agents.

As used herein, "alkyl" refers to a saturated straight, branched, or cyclic hydrocarbon having from about 1 to about 10 carbon atoms (and all combinations and subcombinations of ranges and specific numbers of carbon atoms therein), with from about 1 to about 7 carbon atoms being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "halo" refers to the moiety Cl or F.

As used herein, "cyano" refers to the moiety:

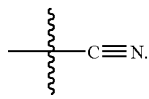

As used herein, "aryl" refers to an optionally substituted, mono- or bicyclic aromatic ring system having from about 5 to about 14 carbon atoms (and all combinations and subcombinations of ranges and specific numbers of carbon atoms therein), with from about 6 to about 10 carbons being preferred. Non-limiting examples include, for example, phenyl and naphthyl.

As used herein, "aralkyl" refers to alkyl radicals bearing an aryl substituent and have from about 6 to about 20 carbon atoms (and all combinations and subcombinations of ranges and specific numbers of carbon atoms therein), with from about 6 to about 12 carbon atoms being preferred. Aralkyl groups can be optionally substituted. Non-limiting examples include, for example, benzyl, naphthylmethyl, diphenylmethyl, triphenylmethyl, phenylethyl, and diphenylethyl.

As used herein, "cycloalkyl" refers to an optionally substituted, alkyl group having one or more rings in their structures having from about 3 to about 14 carbon atoms (and all combinations and subcombinations of ranges and specific numbers of carbon atoms therein), with from about 3 to about 10 carbon atoms being preferred. Multi-ring structures may be bridged or fused ring structures. groups include, but are not limited to, cyclopropyl, cyclobutyl, cyclopentyl, cyclohexyl, cyclooctyl, and adamantyl.

As used herein, "cycloalkylalkyl" refers to alkyl radicals bearing an cycloalkyl substituent and have from about 4 to about 20 carbon atoms (and all combinations and subcombinations of ranges and specific numbers of carbon atoms therein), with from about 6 to about 12 carbon atoms being preferred.

As used herein, the terms "alkoxy" and "alkoxyl" refer to an optionally substituted alkyl-O— group wherein alkyl is as previously defined. Exemplary alkoxy and alkoxyl groups include methoxy, ethoxy, n-propoxy, i-propoxy, n-butoxy, and heptoxy.

As used herein, "carboxy" refers to a —C(=O)OH group.

As used herein, "alkoxycarbonyl" refers to a —C(=O)O-alkyl group, where alkyl is as previously defined.

As used herein, "aroyl" refers to a —C(=O)-aryl group, wherein aryl is as previously defined. Exemplary aroyl groups include benzoyl and naphthoyl.

Typically, substituted chemical moieties include one or more substituents that replace hydrogen. Exemplary substituents include, for example, halo (e.g, F, Cl), alkyl, cycloalkyl, aralkyl, aryl, hydroxyl (—OH), alkoxyl, cyano (—CN), carboxyl (—COOH), —C(=O)O-alkyl, aminocarbonyl (—C(=O)NH$_2$), —N— substituted aminocarbonyl (—C(=O)NHR"), CF$_3$, CF$_2$CF$_3$, and the like. In relation to the aforementioned substituents, each moiety R" can be, independently, any of H, alkyl, cycloalkyl, aryl, or aralkyl, for example.

As used herein, "L-amino acid" refers to any of the naturally occurring levorotatory alpha-amino acids normally present in proteins or the alkyl esters of those alpha-amino acids. The alpha-amino acids include glycine, alanine, valine, leucine, isoleucine, methionine, praline, phenylalanine, tryptophan, asparagine, glutamine, serine, threonine, aspartic acid, glutamic acid, tyrosine, cysteine, lysine, arginine, and histidine.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanedisulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts.

Accordingly, in one embodiment, the invention provides novel pharmaceutically active compounds of formula I:

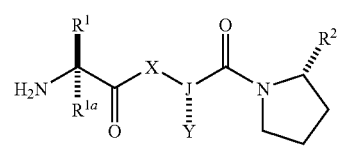

wherein:

$R^1$ is methyl, ethyl, n-propyl, isopropyl, or ethenyl;

$R^{1a}$ is H or methyl;

X is —O—, —S—, —CH₂—, or —NH—, and J is
—CH— or —N—, provided that when J is —N—, X is
—CH₂— or —NH—;

Y is H, methyl, ethyl, n-propyl, or isopropyl;

R² is:

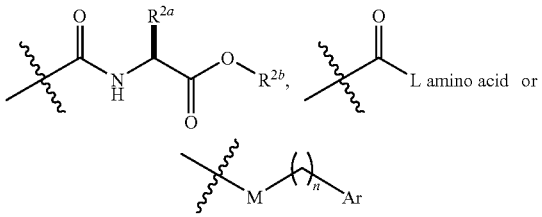

R²ᵃ is aryl, cycloalkyl, optionally substituted aralkyl, or cycloalkylalkyl;
R²ᵇ is H or alkyl;
M is:

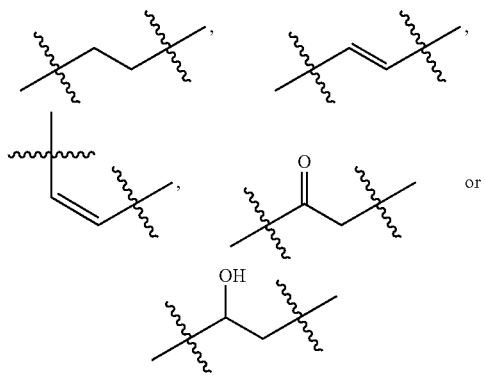

Ar is:

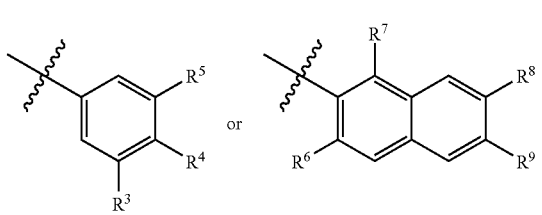

R³, R⁴, R⁵, R⁶, R⁷, R⁸, and R⁹ are each independently H, methyl, ethyl, n-propyl, isopropyl, halo, cyano, —(CH₂)ₚ—C(═O)OH, —(CH₂)ₚ—C(═O)O-alkyl, —(CH₂)ₚ—C(═O)NH₂;

n and p are each independently the integer 0, 1, 2, or 3, and the sum of (n+p) is the integer 2 or 3;

provided that at least one of R³, R⁴, and R5, or at least two of R⁶, R⁷, R⁸, and R⁹ are each independently H, methyl, ethyl, n-propyl, isopropyl, halo, or cyano;

provided that when one or more of R³ and R⁵ is isopropyl, R⁴ is other than isopropyl;

provided that when R⁴ is isopropyl, R³ and R⁵ are each independently other than isopropyl;

provided that when R⁸ is isopropyl, R⁹ is other than isopropyl; and provided that when R¹ᵃ is H, X is —NH—, J is —CH—, Y is H, methyl or isopropyl, and R² is:

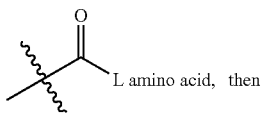

L amino acid, then

R¹ is ethenyl;

or a pharmaceutically acceptable salt thereof.

In some embodiments of formula I compounds, R¹ is methyl, ethyl, or ethenyl. More preferably, R¹ is methyl.

In other embodiments of formula I compounds, R¹ᵃ is H.

In some embodiments of formula I compounds, Y is H, methyl, ethyl, n-propyl or isopropyl. More preferably, Y is H, methyl or isopropyl. Even more preferably, Y is methyl or isopropyl. Still more preferably, Y is isopropyl.

In other embodiments of formula I compounds, Ar is:

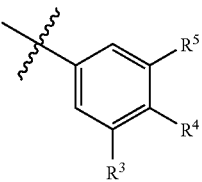

In certain more preferred embodiments of formula I compounds, where Ar is:

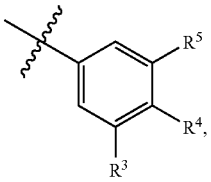

one of R³, R⁴, and R⁵ is —(CH₂)ₚ—C(═O)OH, —(CH₂)ₚ—C(═O)O-alkyl, —(CH₂)ₚ—C(═O)NH₂. More preferably, when one of R³, R⁴, and R⁵ is —(CH₂)ₚ—C(═O)OH, —(CH₂)ₚ—C(═O)O-alkyl, —(CH₂)ₚ—C(═O)NH₂, p is the integer 0. Even more preferably one of one of R³, R⁴, and R⁵ is —(CH₂)ₚ—C(═O)OH or —(CH₂)ₚ—C(═O)O-alkyl. More preferably still, when one of one of R³, R⁴, and R⁵ is —(CH₂)ₚ—C(═O)OH or —(CH₂)ₚ—C(═O)O-alkyl, p is the integer 0. Yet more preferably, one of R³, R⁴, and R⁵ is —(CH₂)ₚ—C(═O)OH. Most preferably, when one of R³, R⁴, and R⁵ is —(CH₂)ₚ—C(═O)OH, p is the integer 0.

In some embodiments of formula I compounds, the sum of (n+p) is the integer 2 or 3. More preferably it is the integer 2.

In some embodiments of formula I compounds wherein R² is

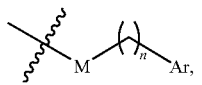

M is preferably

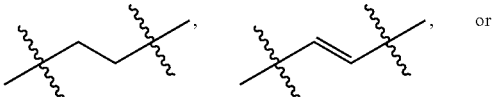

-continued

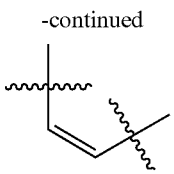

In other embodiments of formula I compounds, Ar is:

[three structures: 4-carboxyphenyl, 4-(alkoxycarbonyl)phenyl, 3-carboxyphenyl]

[structure: 3-(alkoxycarbonyl)phenyl, O-alkyl.]

In yet other embodiments of formula I compounds, $R^2$ is:

[structure with $R^{2a}$ and $OR^{2b}$]

Preferably, $R^{2a}$ is phenyl, cyclohexyl, alpha-naphthylmethyl, beta-naphthylmethyl, benzyl, phenylethyl, or cyclohexylmethyl. Alternately, $R^{2a}$ is aralkyl, more preferably, optionally substituted benzyl, and even more preferably, benzyl substituted with one or more alkyl, halo, aryl, carboxy, alkoxycarbonyl, or aroyl or combinations thereof.

In another embodiment, the invention provides novel pharmaceutically active compounds of formula IIa or IIb:

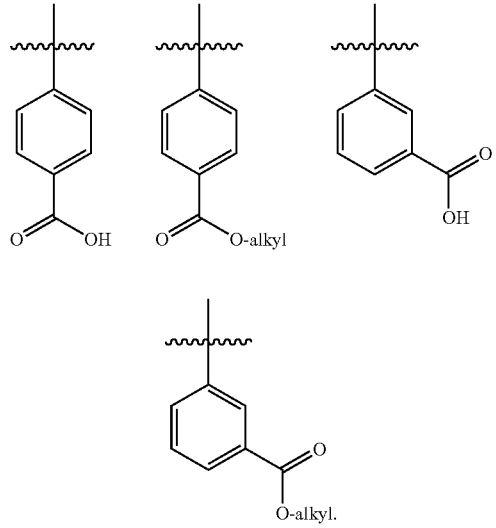

IIa

-continued

IIb wherein:
$R^1$ is methyl, ethyl, n-propyl, isopropyl, or ethenyl;
$R^{1a}$ is H or methyl;
$Q^1$ and $Q^3$ are each independently —O—, —S—, or —NH—;
$Q^2$ is —CH—, or —N—;
$Q^4$ is —N—;
$R^2$ is:

[three structures, third labeled "L amino acid or"]

[structure with M and Ar]

$R^{2a}$ is aryl, cycloalkyl, optionally substituted aralkyl, or cycloalkylalkyl;
$R^{2b}$ is H or alkyl;
M is:

[five structures, last two with O and OH]

Ar is:

[two aryl structures with $R^3, R^4, R^5$ and $R^6, R^7, R^8, R^9$]

$R^3$, $R^4$, $R^5$, R, $R^7$, $R^8$, and $R^9$ are each independently H, methyl, ethyl, n-propyl, isopropyl, halo, cyano, —(CH$_2$)$_p$—C(=O)OH, —(CH$_2$)$_p$—C(=O)O-alkyl, —(CH$_2$)$_p$—C(=O)NH$_2$;
$R^{10}$ is H or methyl;
n and p are each independently the integer 0, 1, 2, or 3, and the sum of (n+p) is the integer 2 or 3;

provided that at least one of $R^3$, $R^4$, and R5, or at least two of $R^6$, $R^7$, $R^8$, and $R^9$ are each independently H, methyl, ethyl, n-propyl, isopropyl, halo, or cyano;

provided that when one or more of $R^3$ and $R^5$ is isopropyl, $R^4$ is other than isopropyl;

provided that when $R^4$ is isopropyl, $R^3$ and $R^5$ are each independently other than isopropyl;

provided that when $R^8$ is isopropyl, $R^9$ is other than isopropyl;

or a pharmaceutically acceptable salt thereof.

In some embodiments of formula IIa or IIb compounds, $R^1$ is methyl, ethyl, or ethenyl. More preferably, $R^1$ is methyl.

In other embodiments of formula IIa or IIb compounds, $R^{1a}$ is H.

In certain embodiments of formula IIa or IIb compounds, Y is H, methyl, or isopropyl. More preferably, it is isopropyl.

In other embodiments of formula IIa or IIb compounds, Ar is:

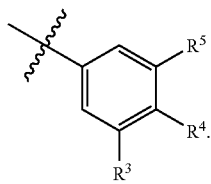

In certain more preferred embodiments of formula IIa or IIb compounds, where Ar is:

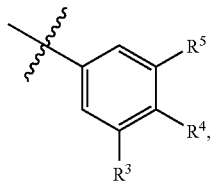

one of $R^3$, $R^4$, and $R^5$ is —(CH$_2$)$_p$—C(=O)OH, —(CH$_2$)$_p$—C(=O)O-alkyl, —(CH$_2$)$_p$—C(=O)NH$_2$. More preferably, when one of $R^3$, $R^4$, and $R^5$ is —(CH$_2$)$_p$—C(=O)OH, —(CH$_2$)$_p$—C(=O)O-alkyl, —(CH$_2$)$_p$—C(=O)NH$_2$, p is the integer 0. Even more preferably one of one of $R^3$, $R^4$, and $R^5$ is —(CH$_2$)$_p$—C(=O)OH or —(CH$_2$)$_p$—C(=O)O-alkyl. More preferably still, when one of one of $R^3$, $R^4$, and $R^5$ is —(CH$_2$)$_p$—C(=O)OH or —(CH$_2$)$_p$—C(=O)O-alkyl, p is the integer 0. Yet more preferably, one of $R^3$, $R^4$, and $R^5$ is —(CH$_2$)$_p$—C(=O)OH. Most preferably, when one of $R^3$, $R^4$, and $R^5$ is —(CH$_2$)$_p$—C(=O)OH, p is the integer 0.

In some embodiments of formula IIa or IIb compounds, the sum of (n+p) is the integer 2 or 3. More preferably it is the integer 2.

In some embodiments of formula IIa or IIb compounds wherein $R^2$ is

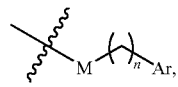

M is preferably

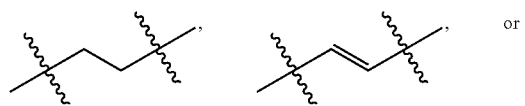

or

In other embodiments of formula IIa or IIb compounds, Ar is:

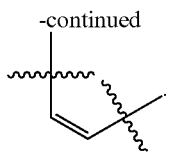

In other embodiments of formula IIa or IIb compounds, Ar is:

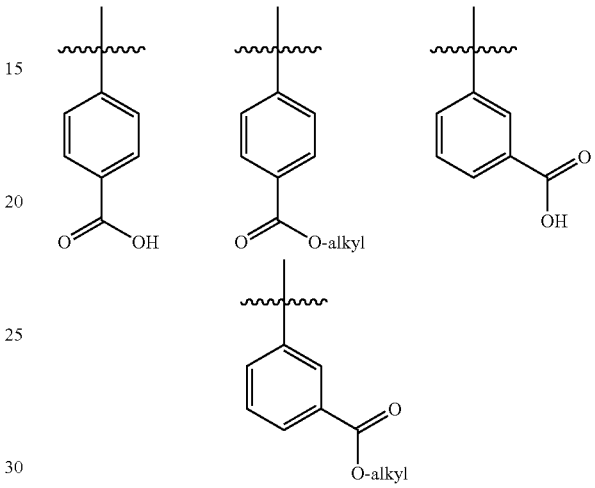

In yet other embodiments of formula I compounds, $R^2$ is:

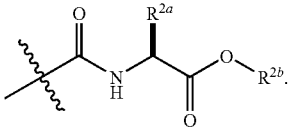

Preferably, $R^{2a}$ is phenyl, cyclohexyl, alpha-naphthylmethyl, beta-naphthylmethyl, benzyl, phenylethyl, or cyclohexylmethyl. Alternately, $R^{2a}$ is aralkyl, more preferably, optionally substituted benzyl, and even more preferably, benzyl substituted with one or more alkyl, halo, aryl, carboxy, alkoxycarbonyl, or aroyl or combinations thereof.

In some embodiments of formula IIa or IIb compounds, $R^{10}$ is H or methyl. Preferably, $R^{10}$ is methyl.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods of the present invention may exist in prodrug form. As used herein, "prodrug" is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, n-propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multi-gram, kilogram, multi-kilogram or commercial industrial scale.

As discussed in detail above, compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The ability of the compounds of the invention to bind IAP is typically measured by an in vitro displacement assay utilizing the BIR3 binding domain and a labeled Smac tetrapeptide analog, such as AVPC-badan dye. Compositions and methods for performing such an assay are described in commonly-owned co-pending International Application No. PCT/US02/17342. Briefly, a protein comprising the BIR3 domain of an IAP is placed in an assay medium comprising a suitable buffer. Preferably, this is a recombinant protein comprising the BIR3 domain, but a full IAP protein also may be used. An aliquot of the AVP-dye is added to the reaction mixture, in the presence of the test compound. Controls comprise the BIR3 and the dye in the absence of the test compound and, optionally, BIR3 and the dye in the presence of the naturally occurring tetrapeptide, AVPI. The fluorescence of the reaction mixture at a selected excitation and emission wavelength, e.g., 387 nm excitation, 545 nm emission, is measured. Alternatively, a emission spectrum is measured at the selected excitation wavelength. In one type of measurement, the test compound is added and an emission spectrum is measured by scanning from, e.g., 460-480 nm. In another type of measurement, the emission intensity at a particular wavelength, e.g., 470 nm, is measured. The emission spectrum of the dye bound to BIR3 is distinctly different from the spectrum of the dye in solution. Thus, the binding affinity of the test compound may be calculated as a function of its ability to displace the dye from the BIR3 domain.

The following examples are provided to describe the invention in greater detail. They are intended to illustrate, not to limit, the invention.

Example 1

Synthesis of Certain Compounds of the Invention and Components Thereof

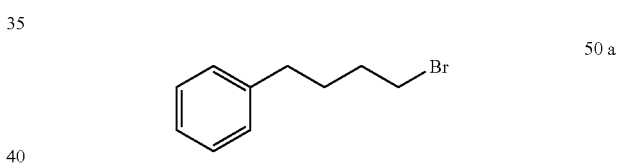

50 a (4-bromo-butyl)-benzene (50 a) (PAA 2-68). Phosphorus tribromide (1.10 mL, 11.2 mmol) was added dropwise to (4-hydroxy-butyl)-benzene (5.04 g, 33.5 mmol) and stirred 1 h under argon at 23° C. The flask was then heated to 100° C. via silicone oil bath and allowed to stir 4 h. The reaction mixture was cooled, quenched with several mL of cold $H_2O$, diluted with ether, washed with brine (2×20 mL), dried over sodium sulfate, and concentrated in vacuo to 6.32 g (88%) of colorless oil. $^1$H NMR (CDCl$_3$, 300 MHz) δ 7.18-7.33 (m, 5H), 3.44 (t, J=6.9 Hz, 2H), 2.66 (t, J=6.9 Hz, 2H), 1.76-1.96 (m, 4H); $^{13}$C NMR (CDCl$_3$, 75 MHz) δ 147.8, 128.4, 125.8, 35.0, 33.7, 32.2, 29.8.

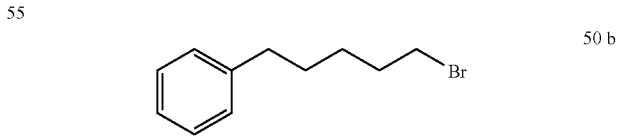

50 b (5-bromo-pentyl)-benzene (50 b) (PAA 67). Phosphorus tribromide (0.47 mL, 5.0 mmol) was added dropwise to (5-hydroxy-pentyl)-benzene (1.98 g, 12.0 mmol) and stirred 1 h under argon at 23° C. The flask was then heated to 100° C. via silicone oil bath and allowed to stir 4 h. The reaction mixture was cooled, quenched with several mL of cold $H_2O$, diluted with ether, washed with brine (2×20 mL), dried over sodium sulfate, and concentrated in vacuo to 2.48 g (91%) of colorless oil. ¹H NMR (CDCl₃, 300 MHz) δ 7.18-7.33 (m, 5H), 3.45 (dt, J=1.8, 6.9 Hz, 2H), 2.68 (t, J=7.2 Hz, 2H), 1.95 (d quintets, J=1.84, 7.2 Hz, 2H), 1.71 (d quintets, J=1.84, 7.2 Hz, 2H), 1.49-1.59 (m, 2H); ¹³C NMR (CDCl₃, 75 MHz) δ 142.2, 128.3, 128.2, 125.7, 35.7, 33.7, 32.6, 30.6, 27.8.

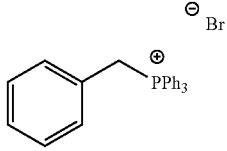

51 a

Phenylmethyl-triphenylphosphonium bromide (51 a) (PAA 59). Triphenylphosphine (2.364 g, 9.00 mmol) was added to benzyl bromide (1.348 g, 8.00 mmol) in 35 mL toluene in a 100-mL round-bottom flask. The mixture was heated to reflux under argon and stirred 24 h, then concentrated in vacuo. The resulting white amorphous solid was triturated with ether (3×20 mL) to yield 3.268 g (94%) white powder. ¹H NMR (CDCl₃, 300 MHz) δ 7.58-7.78 (m, 15H), 7.10-7.26 (m, 5H), 5.34-5.42 (m, 2H).

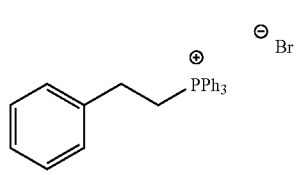

51 b (2-Phenyl-ethyl)-triphenylphosphonium bromide (51 b) (PAA 62). Triphenylphosphine (2.364 g, 9.00 mmol) was added to (2-bromo-ethyl)-benzene (1.496 g, 8.00 mmol) in 35 mL toluene in a 100-mL round-bottom flask. The mixture was heated to reflux under argon and stirred 48 h, then concentrated in vacuo to a thick yellow oil. The oil was dissolved in boiling EtOH under argon. Benzene was added until an oil separated from the solution. The solution was heated under vacuum to remove all solvent and yield 3.6 g (100%) white foam. ¹H NMR (CDCl₃, 300 MHz) δ 7.67-7.91 (m, 15H), 7.17-7.32 (m, 5H), 4.25 (dt, J=12.6, 7.8 Hz, 2H), 3.08 (dt, J=12.9, 7.8 Hz, 2H).

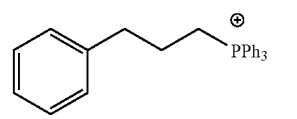

51 c (3-Phenyl-propyl)-triphenylphosphonium bromide (51 c) (PAA 61). Triphenylphosphine (2.364 g, 9.00 mmol) was added to (3-bromo-propyl)-benzene (1.552 g, 8.00 mmol) in 35 mL toluene in a 100-mL round-bottom flask. The mixture was heated to reflux under argon and stirred 48 h, then concentrated in vacuo. The resulting white amorphous solid was triturated with ether (3×20 mL) to yield 1.984 g (55%) white solid. ¹H NMR (CDCl₃, 300 MHz) δ7.66-7.83 (m, 15H), 7.19-7.27 (m, 5H), 3.92-4.02 (m, 2H), 3.06 (t, J=7.2 Hz, 2H), 1.92-2.00 (m, 2H).

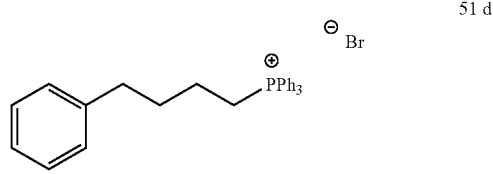

51 d (4-Phenyl-butyl)-triphenylphosphonium bromide (51 d) (PAA 71). Triphenylphosphine (3.932 g, 15.0 mmol) was added to 50 a (3.070 g, 14.4 mmol) in 35 mL toluene in a 100-mL round-bottom flask. The mixture was heated to reflux under argon and stirred 65 h, then concentrated in vacuo to a thick yellow oil. The oil was dissolved in boiling EtOH under argon. Benzene was added until an oil separated from the solution. The solution was heated under vacuum to remove all solvent and yield 6.59 g (96%) white foam. ¹H NMR (CDCl₃, 300 MHz) δ 7.64-7.84 (m, 5H), 7.09-7.20 (m, 5H), 3.81-3.90 (m, 2H), 2.67 (t, J=7.2 Hz, 2H), 2.01 (quintet, 7.2 Hz, 2H), 1.58-1.67 (m, 2H).

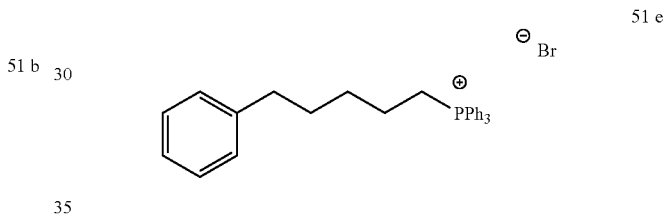

51 e (5-Phenyl-penyl)-triphenylphosphonium bromide (51 e) (PAA 70). Triphenylphosphine (2.620 g, 10.0 mmol) was added to 50 b (1.971 g, 8.70 mmol) in 35 mL toluene in a 100-mL round-bottom flask. The mixture was heated to reflux under argon and stirred 65 h, then concentrated in vacuo to a thick yellow oil. The oil was dissolved in boiling EtOH under argon. Benzene was added until an oil separated from the solution. The solution was heated under vacuum to remove all solvent and yield 3.99 g (94%) white foam. ¹H NMR (CDCl₃, 300 MHz) δ 7.61-7.79 (m, 5H), 7.04-7.29 (m, 5H), 3.63-3.71 (m, 2H), 2.49 (m, 7.2 Hz, 2H, 1.52-1.63 (m, 5H).

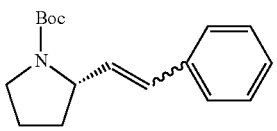

45 a (S)-2-styryl-N-Boc-pyrrolidine (45 a) (PAA 2-18). n-BuLi (0.730 mL, 1.05 mmol) was added dropwise via syringe over 10 minutes to 51 a (0.442 g, 1.021 mmol) in 20 mL THF under argon at −78° C. The mixture was stirred cold for 1 h, then warmed to 23° C. over a 30-minute period. The mixture was immediately cooled back to −78° C. and Boc-L-prolinal (0.200 mL, 1.035 mmol) in 20 mL THF was added dropwise via canula over 5 minutes. The reaction was allowed to stir cold for 1 h, then an additional 24 h at 23° C. The reaction was quenched with several mL's of water, diluted with ethyl acetate, washed with brine (2×25 mL), dried over sodium sulfate, and concentrated in vacuo. Silica gel chromatography (5:1 hexanes/EtOAc) yielded 242 mg (73%) light yellow solid. $R_f$: 0.51 (5:1 hexanes/EtOAc). $^1$H NMR (CDCl$_3$, 300 MHz) δ 7.22-7.37 (m, 5H), 6.38-6.43 (m, 1H), 5.59-6.12 (m, 1H), 4.40-4.74 (m, 1H), 3.47 (br s, 1H), 1.80-2.20 (m, 4H), 1.43 (s, 9H).

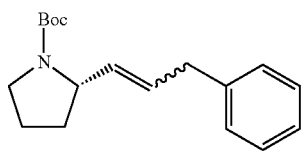

45 b (S)-2-(3-phenyl-propenyl)-N-Boc-pyrrolidine (45 b) (PAA 2-19). n-BuLi (1.2 mL, 1.9 mmol) was added dropwise via syringe over 10 minutes to 51 b (0.769 g, 1.72 mmol) in 20 mL THF under argon at −78° C. The mixture was stirred cold for 1 h, then warmed to 23° C. over a 30-minute period. The mixture was immediately cooled back to −78° C. and Boc-L-prolinal (0.325 mL, 1.72 mmol) in 20 mL THF was added dropwise via canula over 5 minutes. The reaction was allowed to stir cold for 1 h, then an additional 24 h at 23° C. The reaction was quenched with several mL's of water, diluted with ethyl acetate, washed with brine (2×25 mL), dried over sodium sulfate, and concentrated in vacuo. Silica gel chromatography (5:1 hexanes/EtOAc) yielded 330 mg (67%) light yellow oil. Rf: 0.78 (3:1 hexanes/EtOAc). 1H NMR (CDCl$_3$, 300 MHz) δ 7.17-7.32 (m, 5H), 5.43-5.59 (m, 2H), 4.65 (br s, 1H), 3.38-3.57 (m, 4H), 2.08-2.14 (m, 1H), 1.79-1.96 (m, 2H), 1.65-1.73 (m, 1H), 1.47 (s, 9H).

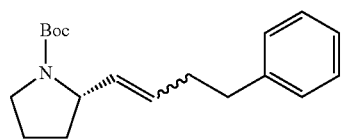

45 c (S)-2-(4-phenyl-but-1-enyl)-N-Boc-pyrrolidine (45 c) (PAA 82). n-BuLi (0.730 mL, 1.05 mmol) was added dropwise via syringe over 10 minutes to 51 c (0.478 g, 1.04 mmol) in 20 mL THF under argon at −78° C. The mixture was stirred cold for 1 h, then warmed to 23° C. over a 30-minute period. The mixture was immediately cooled back to −78° C. and Boc-L-prolinal (0.200 mL, 1.04 mmol) in 20 mL THF was added dropwise via canula over 5 minutes. The reaction was allowed to stir cold for 1 h, then an additional 24 h at 23° C. The reaction was quenched with several mL's of water, diluted with ethyl acetate, washed with brine (2×25 mL), dried over sodium sulfate, and concentrated in vacuo. Silica gel chromatography (5:1 hexanes/EtOAc) yielded 230 mg (73%) light yellow oil. $R_f$: 0.82 (4:1 hexanes/EtOAc). $^1$H NMR (CDCl$_3$, 300 MHz) δ 7.17-7.31 (m, 5H), 5.30-5.39 (m, 2H), 4.43 (br s, 1H), 3.36-3.40 (m, 4H), 2.31-2.82 (m, 4H), 1.72-1.95 (m, 2H), 1.47 (s, 9H).

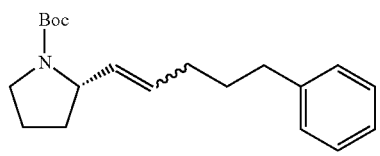

45 d (S)-2-(5-phenyl-pent-1-enyl)-N-Boc-pyrrolidine (45 d) (PAA 82). n-BuLi (0.900 mL, 1.29 mmol) was added dropwise via syringe over 10 minutes to 51 d (0.620 g, 1.29 mmol) in 20 mL THF under argon at −78° C. The mixture was stirred cold for 1 h, then warmed to 23° C. over a 30-minute period. The mixture was immediately cooled back to −78° C. and Boc-L-prolinal (0.250 mL, 1.29 mmol) in 20 mL THF was added dropwise via canula over 5 minutes. The reaction was allowed to stir cold for 1 h, then an additional 24 h at 23° C. The reaction was quenched with several mL's of water, diluted with ethyl acetate, washed with brine (2×25 mL), dried over sodium sulfate, and concentrated in vacuo. Silica gel chromatography (5:1 hexanes/EtOAc) yielded 232 mg (60%) light yellow oil. $R_f$: 0.55 (5:1 hexanes/EtOAc). $^1$H NMR (CDCl$_3$, 300 MHz) δ 7.18-7.31 (m, 5H), 5.36-5.38 (m, 2H), 4.47 (br s, 1H), 3.40 (br s, 1H), 2.64 (t, J=7.2 Hz, 2H), 1.61-2.20 (m, 8H), 1.47 (s, 9H).

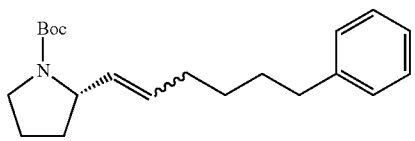

45 e (S)-2-(6-phenyl-hex-1-enyl)-N-Boc-pyrrolidine (45 e) (PAA 81). n-BuLi (0.900 mL, 1.29 mmol) was added dropwise via syringe over 10 minutes to 51 d (0.620 g, 1.29 mmol) in 20 mL THF under argon at −78° C. The mixture was stirred cold for 1 h, then warmed to 23° C. over a 30-minute period. The mixture was immediately cooled back to −78° C. and Boc-L-prolinal (0.250 mL, 1.29 mmol) in 20 mL THF was added dropwise via canula over 5 minutes. The reaction was allowed to stir cold for 1 h, then an additional 24 h at 23° C. The reaction was quenched with several mL's of water, diluted with ethyl acetate, washed with brine (2×25 mL), dried over sodium sulfate, and concentrated in vacuo. Silica gel chromatography (5:1 hexanes/EtOAc) yielded 280 mg (69%) light yellow oil. $R_f$: 0.64 (5:1 hexanes/EtOAc). $^1$H NMR (CDCl$_3$, 300 MHz) δ 7.17-7.32 (m, 5H), 5.29-5.34 (m, 2H), 4.49 (br s, 1H), 3.38-3.42 (m, 2H), 2.63 (t, J=7.2 Hz, 2H), 1.38-2.11 (m, 10H), 1.44 (s, 9H).

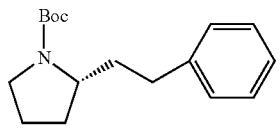

44 a (S)-2-phenethyl-N-Boc-pyrrolidine (44 a) (PAA 2-28). A 10-mL round-bottom flask fitted with a 3-way tap and balloon was charged with 160 mg of 10% Pd—C. The flask was evacuated and filled with hydrogen gas 10 times. EtOH (5 mL) was added via syringe and stirred for several minutes. Alkene 45 a (260 mg,) in 2 mL EtOH was added via syringe and stirred for 24 h. Hydrogen gas was added as the balloon deflated. Upon complete reaction the catalyst was removed by filtration. The product was concentrated in vacuo to yield 251 mg (97%) of colorless oil. $^1$H NMR (CDCl$_3$, 300 MHz) δ 7.19-7.30 (m, 5H), 3.76-3.88 (br m, 1H), 3.34-3.43 (br m, 2H), 2.59-2.62 (m, 2H), 1.62-2.16 (m, 6H), 1.46 (s, 9H).

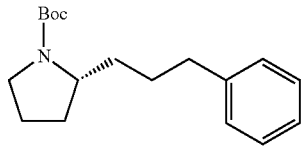

44 b

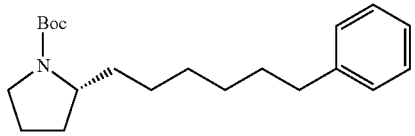

44 e (S)-3-phenpropyl-N-Boc-pyrrolidine (44 b) (PAA 2-29). A 10-mL round-bottom flask fitted with a 3-way tap and balloon was charged with 157 mg of 10% Pd—C. The flask was evacuated and filled with hydrogen gas 10 times. EtOH (5 mL) was added via syringe and stirred for several minutes. Alkene 45 b (145 mg,) in 2 mL EtOH was added via syringe and stirred for 24 h. Hydrogen gas was added as the balloon deflated. Upon complete reaction the catalyst was removed by filtration. The product was concentrated in vacuo to yield 149 mg (100%) of colorless oil. $^1$H NMR (CDCl$_3$, 300 MHz) δ 7.16-7.30 (m, 5H), 3.71-3.83 (br m, 1H), 3.30-3.39 (br m, 2H), 2.60 (t, J=7.2 Hz, 2H), 1.62-1.90 (m, 5H), 1.46 (s, 9H), 1.29-1.42 (m, 3H).

(S)-6-phenhexyl-N-Boc-pyrrolidine (44 e) (PAA 2-27). A 10-mL round-bottom flask fitted with a 3-way tap and balloon was charged with 151 mg of 10% Pd—C. The flask was evacuated and filled with hydrogen gas 10 times. EtOH (3 mL) was added via syringe and stirred for several minutes. Alkene 45 e (301 mg,) in 2 mL EtOH was added via syringe and stirred for 24 h. Hydrogen gas was added as the balloon deflated. Upon complete reaction the catalyst was removed by filtration. The product was concentrated in vacuo to yield 285 mg (95%) of colorless oil. $^1$H NMR (CDCl$_3$, 300 MHz) δ 7.17-7.30 (m, 5H), 3.69-3.76 (br m, 1H), 3.30-3.39 (m, 2H), 2.61 (7, J=7.6 Hz, 2H), 1.73-1.90 (m, 3H), 1.62-1.64 (m, 3H), 1.47 (s, 9H), 1.28-1.43 (m, 8H).

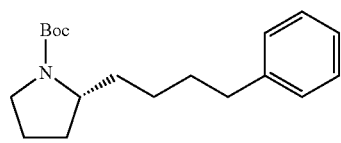

44 c (S)-4-phenbutyl-N-Boc-pyrrolidine (44 c) (PAA 2-160). A 50-mL round-bottom flask fitted with a 3-way tap and balloon was charged with 400 mg of 10% Pd—C. The syringe and stirred for several minutes. Alkene 45 c (405 mg,) in 5 mL EtOH was added via syringe and stirred for 2 h. Hydrogen gas was added as the balloon deflated. Upon complete reaction the catalyst was removed by filtration. The product was concentrated in vacuo to yield 376 mg (93%) of colorless oil. $^1$H NMR (CDCl$_3$, 300 MHz) δ 7.15-7.31 (m, 5H), 3.70-3.76 (br m, 1H), 3.26-3.41 (m, 2H), 2.58-2.64 (m, 2H), 1.59-1.93 (m, 7H), 1.49 (s, 9H), 1.30-1.35 (m, 3H).

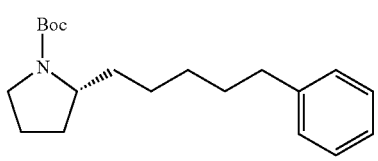

44 d (S)-5-phenpentyl-N-Boc-pyrrolidine (44 d) (PAA 2-27). A 10-mL round-bottom flask fitted with a 3-way tap and balloon was charged with 100 mg of 10% Pd—C. The flask was evacuated and filled with hydrogen gas 10 times. EtOH (3 mL) was added via syringe and stirred for several minutes. Alkene 45 d (100 mg,) in 2 mL EtOH was added via syringe and stirred for 24 h. Hydrogen gas was added as the balloon deflated. Upon complete reaction the catalyst was removed by filtration. The product was concentrated in vacuo to yield 93.7 mg (94%) of colorless oil. $^1$H NMR (CDCl$_3$, 300 MHz) δ 7.17-7.31 (m, 5H), 3.70-3.76 (br m, 1H), 3.30-3.40 (m, 2H), 2.61 (7, J=8.0 Hz, 2H), 1.73-1.90 (m, 3H), 1.59-1.65 (m, 3H), 1.47 (s, 9H), 1.29-1.40 (m, 6H).

53

Boc-Ala-Val-OMe (53) (PAA 2-7). EDC (1.521 g, 7.93 mmol) was added to Boc-Ala (1.500 g, 7.93 mmol) in 25 mL chloroform at 0° C. and the mixture was allowed to stir 30 minutes. Valine methyl ester (1.329 g, 7.93 mmol), triethylamine (1.11 mL, 7.93 mmol) and 25 mL chloroform were combined in a separate 50-mL flask and stirred. This mixture was transferred to the solution of activated Boc-alanine and stirred at 0° C. for 3 h. The ice bath was removed and the reaction mixture stirred an additional 27 h. Three drops of acetic acid were added and the stirring continued for 15 minutes. The mixture was concentrates in vacuo and then redissolved in EtOAc (50 mL). The organic portion was washed with 10% NaHCO$_3$ (2×25 mL), 1N HCl (2×25 mL), water (25 mL), dried over sodium sulfate, and concentrated in vacuo to 1.848 g (81%) of product. $^1$H NMR (CDCl$_3$, 300 MHz) δ 6.68 (br d, J=5.4 Hz, 1H), 4.99 (br s, 1H), 4.53 (dd, J=4.8, 8.7 Hz, 1H), 4.19 (br t, J=7.5 Hz, 1H), 3.74 (s, 3H), 2.18 (septet, J=6.9 Hz, 1H), 1.45 (s, 9H), 0.93 (d, J=6.9 Hz, 3H), 0.90 (d, J=6.9 Hz, 3H).

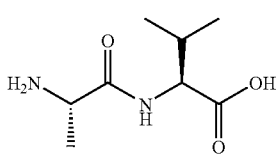

54

Boc-Ala-Val-OH (54) (PAA 2-32). Boc-Ala-Val-OMe 53 (1.750 g, 5.79 mmol) was stirred in 40 mL acetone. NaOH solution (8.7 mL of 2.0 M aqueous solution) was added and stirred 2 h at 23° C. Acetone was removed under reduced pressure and the resulting solution was diluted with EtOAc (20 mL). The organic fraction was washed with water (2×20 mL), dried over sodium sulfate, and concentrated in vacuo to yield 1.561 g (99%) product. $^1$H NMR (CDCl$_3$, 300 MHz) δ 12.28 (br s, 1H), 7.69 (d, J=8.7 Hz, 1H), 6.98 (d, J=7.5 Hz, 1H), 4.15 (dd, J=5.4, 8.4 Hz, 1H), 4.04 (quintet, J=7.2 Hz, 1H), 3.35 (br s, 2H), 2.04 (octet, J=6.6 Hz, 1H), 1.37 (s, 9H), 1.16 (d, J=7.2 Hz, 3H), 0.87 (d, J=7.2 Hz, 3H); $^{13}$C NMR (CDCl$_3$, 75 MHz) δ 172.9, 155.1, 78.1, 56.8, 30.2, 28.2, 19.0, 18.0, 17.8.

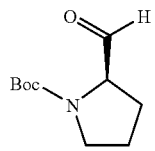

38

Boc-L-Prolinal (38) (PAA 2-226). Boc-L-proline (20.0 g, 92.9 mmol) was combined with 200 mL THF in a 500 mL flask fitted with a reflux condenser. Borane methyl sulfide complex (70 mL, 140 mmol) was added over a 30 minute period at 0° C. under argon. When gas evolution ceased the flask was heated to reflux via silcone oil bath and stirred 1 h. The reaction was cooled to 23° C. and quenched slowly with MeOH. An additional 100 mL of MeOH was added and then concentrated in vacuo. The reaction mixture was redissolved and concentrated with 200 mL MeOH and then 2×100 mL of toluene. The sample was concentrated on the vacuum pump overnight to yield 18.78 g of white solid alcohol product. This material was dissolved in 200 mL dichloromethane and stirred under argon. PCC (28 g, 141 mmol) followed by 4 Å molecular sieves (35 g) and 1 ml AcOH were added to the mixture at 0° C. The reaction mixture was allowed to stir 2.5 h at 23° C. The flask was filled with ether then filtered over a small bed of silica gel. Silica gel chromatography afforded 13.1 g (70% over two steps) of colorless oil. R$_f$: 0.39 (5:1 hexanes/EtOAc). $^1$H NMR (CDCl$_3$, 300 MHz) δ 9.46-9.56 (m, 1H), 4.03-4.21 (m, 1H), 3.43-3.58 (m, 2H), 1.87-2.14 (m, 4H), 1.43-1.48 (m, 9H).

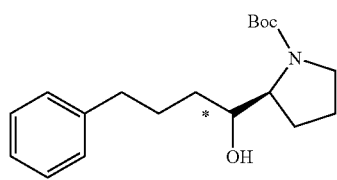

57 + 58

(S)-2-(1-Hydroxy-4-phenyl-butyl)-N-Boc-pyrrolidine (57 and 58) (PAA 2-138). Mg turnings (1.6 g, 67 mmol) was stirred under argon in 34 mL of ether. (3-bromo-propyl)-benzene (8 mL, 52 mmol) in 10 mL of ether was added slowly to minimize boiling of the solvent. After 1 h, the resulting Grignard solution was transferred away from excess magnesium via canula and stored under argon. A flask was charged with 16 mL of 1.25 M Grignard solution and cooled to 0° C. under argon. Prolinal (1.529 g, 7.7 mmol) in 10 mL ether was transferred dropwise to the flask via syringe over 10 min. The rxn. was stirred 1 h, then the ice bath was removed and the mixture was stirred an additional 3 h. The reaction was quenched slowly with several mL's of saturated NH$_4$Cl, extracted with 50 mL ether, dried over sodium sulfate, and concentrated in vacuo. Silica gel chromatography (5:1 hexanes/EtOAc) allowed for separation of the diastereomers, 0.98 g oil and 0.63 g solid (overall 67% yield). R$_f$: 0.32 (5:1 hexanes/EtOAc). $^1$H NMR (CDCl$_3$, 300 MHz) δ; $^{13}$C NMR (CDCl$_3$, 75 MHz) δ 142.4, 128.4, 128.2, 125.6, 80.4, 75.2, 62.6, 47.1, 35.8, 34.2, 28.5, 28.4, 26.7, 24.0. R$_f$: 0.28 (5:1 hexanes/EtOAc). $^1$H NMR (CDCl$_3$, 300 MHz) δ; $^{13}$C NMR (CDCl$_3$, 75 MHz) δ 124.4, 128.4, 128.2, 125.6, 79.8, 73.0, 62.8, 47.9, 35.8, 34.2, 32.0, 28.5, 28.4, 27.8, 24.2.

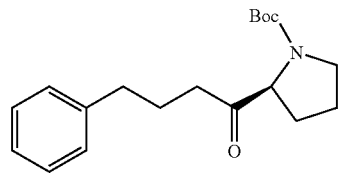

59

(S)-2-(40phenyl-butyryl)-N-Boc-pyrrolidine (59) (PAA 2-245). A mixture of alcohols 57 and 58 (0.77 g, 2.4 mmol) were stirred in 25 mL dichloromethane and stirred under argon. PCC (0.8 g, 3.6 mmol) followed by 4 Å molecular sieves (0.8 g) and several drops AcOH were added to the mixture at 0° C. The reaction mixture was allowed to stir 48 h at 23° C. The flask was filled with ether then filtered over a small bed of silica gel and concentrated. The resulting oil was stirred in saturated sodium bisulfite 1 h. The product was extracted with dichloromethane and concentrated in vacuo to yield 588 mg (77%) of white, unpleasant smelling solid. R$_f$: 0.32 (5:1 hexanes/EtOAc). $^1$H NMR (CDCl$_3$, 300 MHz) δ 7.17-7.30 (m, 5H), 4.33 (dd, J=4.4, 8.8 Hz)+4.21 (dd, J=5.2, 8.8 Hz) 1H, 3.40-3.55 (m, 2H), 2.60-2.66 (m, 2H), 2.39-2.53 (m, 2H), 2.06-2.18 (m, 1H), 1.93 (quintet, J=7.2 Hz, 1H), 1.74-1.86 (m, 3H), 1.532+1.37 (s, 9H); $^{13}$C NMR (CDCl$_3$, 75 MHz) δ 209.9, 154.5, 153.8, 141.6, 141.3, 128.4, 128.3, 128.2, 125.9, 125.8, 80.0, 79.7, 65.1, 64.6, 46.8, 46.6, 38.4, 37.5, 35.0, 29.9, 28.8, 28.4, 28.2, 24.6, 24.6, 24.3, 23.6

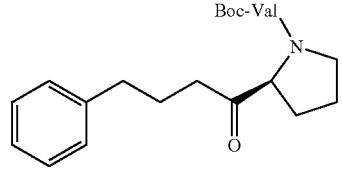

60

(S)-2-(4-phenyl-butyryl)-Boc-Val-pyrrolidine (60) (PAA 2-211). Ketone 59 was stirred in 50:50 TFA/dichloromethane for 2 hours. After removal of solvent, the resulting TFA amine salt (0.784 mmol) was combined with Boc-Val-OH (170 mg, 0.784 mmol), NEt$_3$ (0.330 mL, 2.35 mmol), BOP-Cl (300 mg, 1.18 mmol) in 15 mL of dichloromethane at 0° C. under argon. The reaction mixture was allowed to stir 24 h, then washed with 1N HCl (10 mL), saturated NaHCO$_3$ (10 mL), and brine (20 ml). The organic fraction was dried over sodium sulfate and concentrated in vacuo. Silica gel chromatography (50:50 hexanes/ether) yielded 226 mg (71%) of colorless oil. R$_f$: 0.32 (50:50 hexanes/ether). $^1$H NMR (CDCl$_3$, 300 MHz) δ 7.13-7.27 (m, 5H), 5.20 (d, J=9.3 Hz, 1H), 4.55 (dd, J=6.0, 8.4 Hz) 1H, 4.25 (dd, J=6.0, 9.3 Hz, 1H), 3.71-3.77 (m, 1H), 2.39-2.62 (m, 4H), 1.89-2.12 (m, 6H), 1.71 (septet, J=6.6 Hz, 1H), 1.40 (s, 9H), 1.00 (d, J=6.6 Hz, 3H), 0.90 (d, J=6.6 Hz, 3H); $^{13}$C NMR (CDCl$_3$, 75 MHz) δ 208.0, 170.7, 156.7, 141.4, 128.3, 128.2, 125.7, 64.2, 56.5, 47.2, 39.3, 34.8, 31.1, 28.1, 27.9, 24.8, 24.6, 19.2, 17.2.

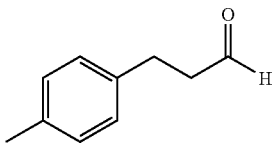

63 a

3-p-tolyl-propionaldehyde (63 a) (PAA 2-259). A flask was charged with p-iodotoluene (2.18 g, 10. mmol), allyl alcohol (1.0 mL, 15 mmol), sodium bicarbonate (1.68 g, 20 mmol), tetrabutyl ammonium chloride (2.78 g, 10.0 mmol), palladium acetate (45 mg, 2 mol %) and 10 mL DMF. The mixture was stirred under argon at 40° C. for 18 h. The reaction mixture as cooled, diluted with ether, and filtered over Celite. Silica gel chromatography (5:1 hexanes/EtOAc) yielded g (%) of yellow oil. $R_f$: 0.47 (3:1 hexanes/ether). $^1$H NMR (CDCl$_3$, 300 MHz) δ; $^{13}$C NMR (CDCl$_3$, 75 MHz) δ

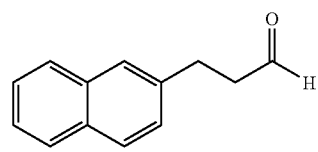

63 b

3-Naphthalene-2-yl-propionaldehyde (63 b) (PAA 2-260). A flask was charged with 2-iodo-naphthalene (2.095 g, 8.25 mmol), allyl alcohol (0.83 mL, 12.38 mmol), sodium bicarbonate (1.39 g, 16.5 mmol), tetrabutyl ammonium chloride (8.25 mmol), palladium acetate (37 mg, 2 mol %) and 10 mL DMF. The mixture was stirred under argon at 40° C. for 18 h. The reaction mixture as cooled, diluted with ether, and filtered over Celite. Silica gel chromatography (5:1 hexanes/EtOAc) yielded 1.23 g (67%) of yellow oil. $R_f$: 0.40 (3:1 hexanes/ether). $^1$H NMR (CDCl$_3$, 300 MHz) δ 9.87 (t, J=1.2 Hz, 1H), 7.80-7.85 (m, 3H), 7.65 (s, 1H), 7.46-7.50 (m, 2H), 7.35 (dd, 1.8, 8.7 Hz, 1H), 3.14 (t, J=7.5 Hz, 2H), 2.87 (ddt, 0.6, 1.2, 7.5 Hz, 2H); $^{13}$C NMR (CDCl$_3$, 75 MHz) δ 201.4, 137.8, 133.5, 132.1, 128.2, 127.6, 127.4, 126.8, 126.4, 126.1, 125.4, 45.1, 28.2.

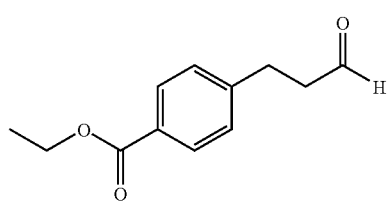

63 c

4-(3-oxo-propyl)-benzoic acid ethyl ester (63 c) (PAA 2-264). A flask was charged with p-iodobenzoic acid ethyl ester (2.78 g, 10.0 mmol), allyl alcohol (1.0 mL, 15. mmol), sodium bicarbonate (1.68 g, 20 mmol), tetrabutyl ammonium chloride (2.78 g, 10.0 mmol), palladium acetate (37 mg, 2 mol %) and 10 mL DMF. The mixture was stirred under argon at 40° C. for 18 h. The reaction mixture as cooled, diluted with ether, and filtered over Celite. Silica gel chromatography (5:1 hexanes/EtOAc) yielded 1.27 g (61%) of yellow oil. $R_f$: 0.33 (5:1 hexanes/ether). $^1$H NMR (CDCl$_3$, 300 MHz) δ 9.83 (t, J=0.9 Hz, 1H), 7.94 (d, J=8.4 Hz, 2H), 7.27 (d, 8.4 Hz, 2H), 4.37 (quartet, J=7.2 Hz, 2H), 3.02 (t, J=7.5 Hz, 2H), 2.82 (d, J=7.5 Hz, 2H), 1.39 (t, 7.2 Hz, 3H).

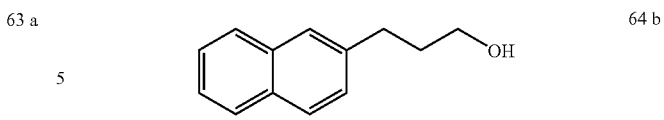

64 b

3-Naphthalene-2-yl-propanol (64 b) (PAA 2-266). Sodium borohydride (53 mg, 1.36 mmol) was added to 63 b in 10 mL EtOH under argon. The mixture was allowed to stir 10 h at 23° C. The reaction was quenched with dilute acetic acid. The reaction mixture was diluted with EtOAc, washed with water (2×20 mL), dried over sodium sulfate, and concentrated in vacuo to yield 470 mg (94%) of light brown solid. $^1$H NMR (CDCl$_3$, 300 MHz) δ 7.78-7.83 (m, 3H), 7.65 (d, 8.4 Hz, 2H), 7.43-7.47 (m, 2 h), 7.35-7.37 (m, 1H), 3.74-3.90 (m, 2H), 2.89 (t, J=6.9 Hz, 2H), 2.00 (quintet, J=6.9 Hz, 2H).

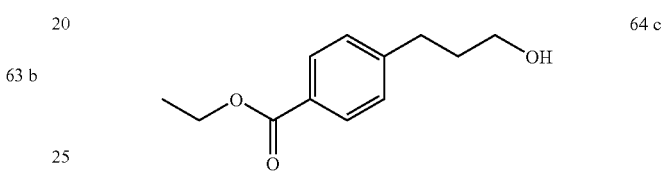

64 c

4-(3-hydroxy-propyl)-benzoic acid ethyl ester (64 c) (PAA 2-267). Sodium borohydride (47 mg, 1.21 mmol) was added to 63 c (500 mg, 2.42 mmol) in 10 mL EtOH under argon. The mixture was allowed to stir 10 h at 23° C. The reaction was quenched with dilute acetic acid. The reaction mixture was diluted with EtOAc, washed with water (2×20 mL), dried over sodium sulfate, and concentrated in vacuo to yield 422 mg (85%) of colorless oil. $^1$H NMR (CDCl$_3$, 300 MHz) δ 7.96 (d, J=8.4 Hz, 2H), 7.25-7.27 (m, 2H), 4.36 (quartet, J=6.9 Hz, 2H), 3.68 (t, J=6.0 Hz, 2H), 2.75 (quintet, J=6.9 Hz, 2H), 2.09 (s, 1H), 1.93 (quintet, J=6.9 Hz, 2H), 1.39 (t, 6.0 Hz, 3H).

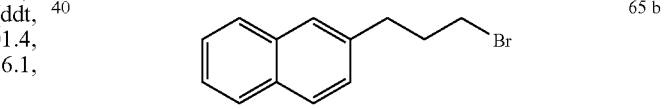

65 b

2-(3-bromo-propyl)naphthalene (65 b) (PAA 2-271). PBr$_3$ (60 μL, 0.53 mmol) was added via syringe to 64b (246 mg, 1.32 mmol) in 1 ml toluene under argon at 0° C. The mixture was stirred overnight, then heated to reflux for 16 h. The mixture was cooled, washed with water (5 mL), brine (5 mL), dried over sodium sulfate, and concentrated in vacuo. $^1$H NMR (CDCl$_3$, 300 MHz) δ 7.81-7.86 (m, 3H), 7.68 (d, 8.4 Hz, 2H), 7.44-7.53 (m, 2 h), 7.37 (dd, J=1.5, 8.4 Hz, 1H), 3.45 (t, J=6.6 Hz, 2H), 2.98 (t, J=7.2 Hz, 2H), 2.29 (quintet, J=6.6 Hz, 2H); $^{13}$C NMR (CDCl$_3$, 75 MHz) δ 137.9, 133.5, 132.1, 128.1, 127.1, 126.7, 126.0, 125.3, 34.1, 34.0, 33.1.

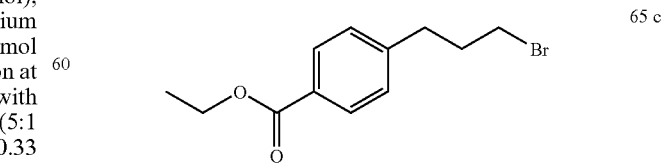

65 c

4-(3-bromo-propyl)-benzoic acid ethyl ester (65 c) (PAA 2-272). PBr$_3$ (40 μL, 0.34 mmol) was added via syringe to 64b (175 mg, 0.84 mmol) in 1 ml toluene under argon at 0° C. The mixture was stirred overnight, then heated to reflux for 16 h. The mixture was cooled, washed with water (5 mL), brine (5 mL), dried over sodium sulfate, and concentrated in vacuo. $^1$H NMR (CDCl$_3$, 300 MHz) δ 8.01 (d, J=7.8 Hz, 2H), 7.29-7.31 (m, 2H), 4.40 (quartet, J=6.9 Hz, 2H), 3.42 (t, J=6.6 Hz, 2H), 2.87 (quintet, J=7.2 Hz, 2H), 2.21 (quintet, J=6.6 Hz, 2H), 1.42 (t, J=6.6 Hz, 3H); $^{13}$C NMR (CDCl$_3$, 75 MHz) δ 166.5, 145.8, 129.8, 128.5, 128.4, 60.8, 33.9, 33.7, 32.7, 14.3.

Example 2

Synthesis of Certain Oxazole Compounds

Synthetic Scheme for Oxazole Compounds

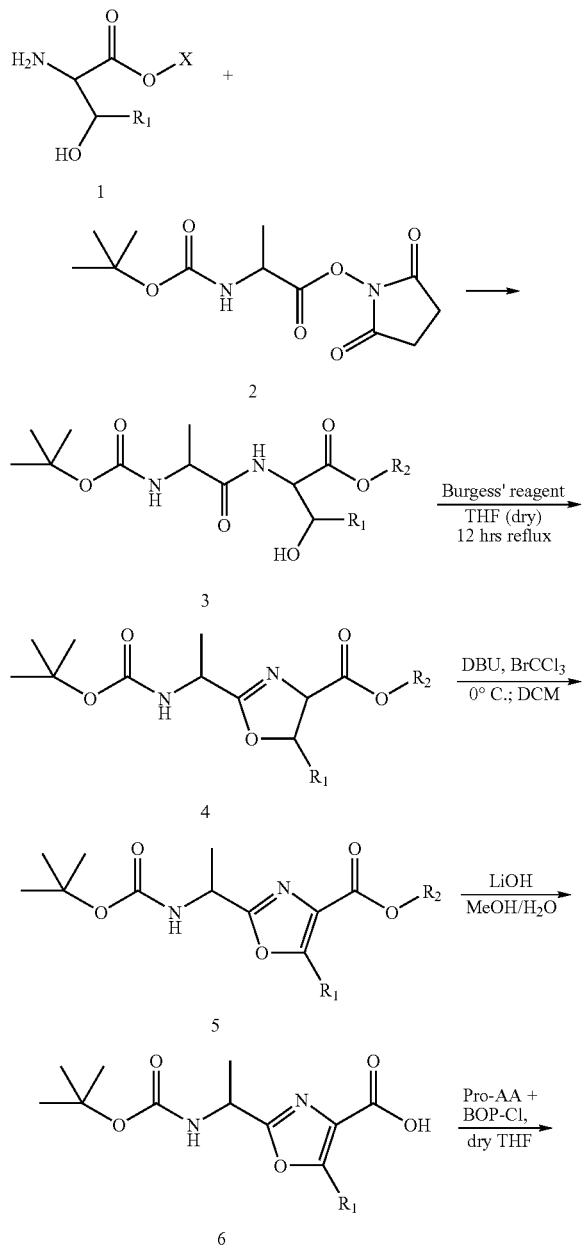

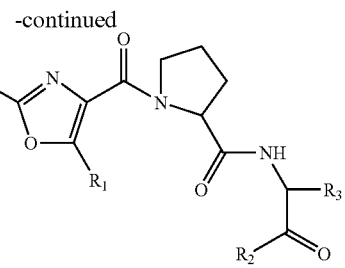

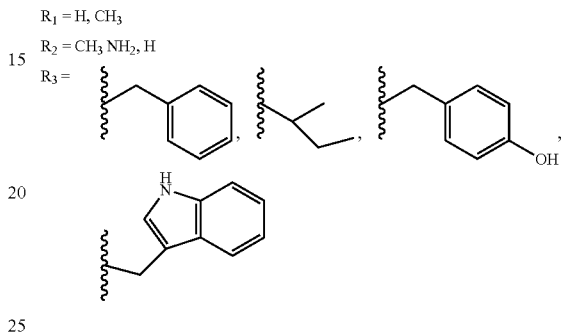

I. Formation of Boc-Ala-Ser-OMe (3):

1 eq. of Boc-Ala-succinimide ester (2) was added to an ice-cold solution of DIPEA (2 eq.) and H-Ser-methyl ester hydrochloride (R=H) or H-Thr-methyl ester hydrochloride (R=CH3) (1) in dry THF under argon. The solution was allowed to warm to RT and stirred overnight (Rocchi, R. et al. (1987) *Int. J. Peptide Protein Res.* 30, 240-256). The THF was removed in vacuo, the resin was brought up in ethyl acetate and washed three times each with saturated sodium bicarbonate, 5% citric acid and saturated sodium chloride. The solution was dried with magnesium sulfate and the solvent was removed in vacuo leaving a white solid. Single spot on TLC (1:10 MeOH/CHCl$_3$). No purification was necessary. 75% yield.

II. Formation of Boc-Ala-Ser-OMe oxazoline (4):

1.05 eq. Burgess' reagent was added in one portion to a stirred solution of 3 in dry THF and the resulting solution was then heated at 70° C. for 12 h under an argon atmosphere (Mink et al., (1998) *Tetrahedron Lett.* 39, 5709-5712). The reaction was worked up as described in I above. The product was purified by a silica gel column in 70/30 ethyl acetate/hexanes. 25% yield.

II. Formation of Boc-Ala-Ser-OMe oxazole (5):

A solution of 4 in CH$_2$Cl$_2$ was cooled to 0° C. and 1.1 eq. of DBU was added. 1.1 eq. of bromotrichloromethane was introduced dropwise via syringe over 10 min. The reaction was stirred under argon until completion (8 hrs). The product was purified by a silica gel column in 30 to 50% ethyl acetate in hexane. 55% yield.

IV. Deprotection of Carboxylic Acid of Boc-Ala-Ser-OMe Oxazole (6):

2.3 eq. of LiOH monohydrate was added to a stirred solution of 5 in MeOH:H2O (3:1) at 0° C. The solution was stirred with gradual warming to room temperature, until reaction was complete (monitored by TLC in 1:10 MeOH/CHCl$_3$) (Aquilar, E. and Meyers, A. (1994) *Tetrahedron Lett.* 35, 2472-2480).

V. Formation of Boc-Ala-Ser-Pro-AA-OMe Oxazole (7)

Pro-AA (where AA is phenylalanine, isoleucine, tyrosine or tryptophan) was synthesized as in I and AA-NH2 or AA-OMe was used to yield the amide, the methyl ester or free acid, respectively. 1.1 eq. of Pro-Phe and 3 eq. of DIPEA were dissolved in dry THF and added to a solution of 6 and 1.4 eq. of BOP-Cl at 0° C. (Palomo-Coll, A. L. and Diago-Meseguer, J. (1980) *Synthesis.* 7, 547-551). The reaction was stirred for 12-14 hrs under Ar. The Boc was TFA deprotected. Then, the Phe-OMe was deprotected as in W. The methyl ester, amide and free acid were purified by HPLC and characterized by mass spectrometry and $^1$H NMR.

Synthetic Scheme for Non-Peptidic Oxazole Analogs:

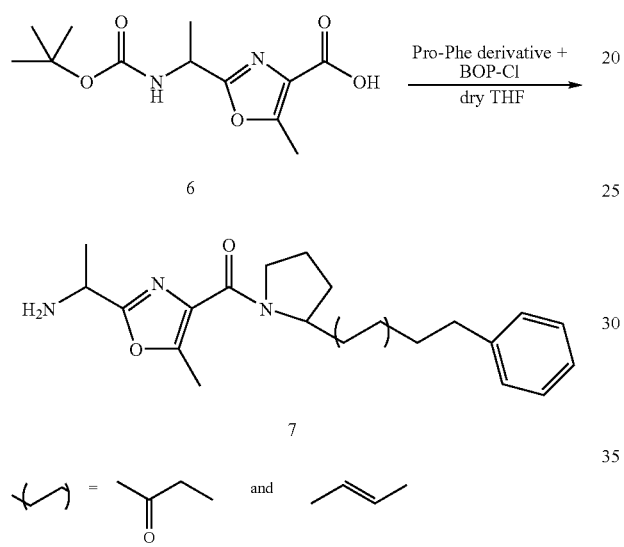

The coupling reaction between the oxazole analog and the Pro-Phe analogs was carried out as in V above. The compounds were purified by HPLC and characterized by mass spectrometry and $^1$H NMR.

Example 3

Synthesis of Compounds Containing Proline or Phenylalanine Derivatives

Materials. Unless otherwise stated, materials were purchased from Aldrich Chemical Co. (Milwaukee, Wis.) or Fisher Scientific (Pittsburgh, Pa.) and used without further purification. All unnatural phenylalanine derivatives were purchased from Advanced ChemTech (Louisville, Ky.) or Novabiochem (Calbiochem, San Diego, Calif.) as the Fmoc protected amino acid. These and the proline derivatives were used in peptide synthesis in the same manner as a naturally-occurring amino acid would be. Methylbenzhydrylamine (MBHA) solid-phase peptide synthesis resin, Rink amide resin, and 9-Fluorenylmethoxycarbonyl (Fmoc) protected amino acids were obtained from Advanced ChemTech (Louisville, Ky.) and NovaBiochem (San Diego, Calif.). 6-Bromoacetyl-2-dimethylaminonaphthalene (badan) dye was obtained from Molecular Probes (Eugene, Oreg.).

Peptide synthesis. Peptide molecules were synthesized on an Advanced ChemTech 396 MPS automated peptide synthesizer by Fmoc protocol on Rink amide resin. The side chains of the amino acids that are sensitive to side reactions were protected as follows: the hydroxy groups on the 4-hydroxy-proline and on the p-carboxy substituted phenylalanine were t-butyl protected and a pentamethyldihydrobenzofuran group was used to protect the arginine. After the final amino acid was added, deprotection and cleavage of the peptides from the resin was effected by adding 1 ml of a 95% TFA, 2.5% water, and 2.5% triisopropylsilane (TIS) solution to each well, and shaking for 1 hour. The cleavage solution was collected and a further 0.5 ml of the cleavage solution was added to each well and mixed for another hour. The combined cleavage solutions were added to 20 ml of water, lyophilized to dryness, then taken up in 5 ml of water before being filtered through syringe filters (0.2 µm) and lyophilized again. Peptides containing proline derivatives were purified by HPLC on a Vydac C18 preparative scale column. The presence of the desired molecules was confirmed by mass spectroscopy.

Example 4

Assays

Test compounds were reconstituted in water and test solutions were made that were approximately 200 µM in the test compounds. Exact concentrations were determined for 10 representative test solutions for the phenylalnine library, and for all members of the proline and oxazole libraries. Concentrations were determined by $^1$H-NMR using a dioxane solution of known concentration as an external reference. The concentrations of the other peptide solutions from the phenylalanine library were taken to be the average value of the known solutions from the same library synthesis.

Concentrations of the methylene bridged compounds were estimated using the molar absorptivity of a phenyl ring in water at 250 nm ($\epsilon$=200 M$^{-1}$cm$^{-1}$). These compounds were not soluble in water, so they were taken up in an aqueous 10% dimethylsulfoxide (DMSO) solution. The assay solution was then approximately 1% DMSO, which had no effect on the observed emission at that concentration.

Fluorescence protocol. Luminescence spectra were recorded using a Photon Technologies, Inc. fluorometer with a Xe arc lamp and a PMT detector. The absorbance of all solutions was less than 0.2 at the excitation wavelength (387 nm). The buffer used in all of the fluorescence experiments was 50 mM potassium phosphate, 100 mM NaCl, 2 mM 1,4-dithio-DL-threitol (DTT), pH 7.

Assay of Test Compounds. The samples were prepared in a 96 well plate lined with glass tubes, to prevent adsorption of the dye to plastic. The plate was stored on ice in the dark between measurements. A small volume cuvette, with a path length of 2 mm, was used to collect the emission spectra. A 44

µM aqueous solution of AVPC-badan, a 63 µM BIR3 solution, and buffer were mixed to give a stock solution which was 5.6 µM in both AVPC-badan and BIR3. 390 µL of this stock solution were added to each well on the 96 well plate. 50 µL of the test compound solutions were added and mixed immediately prior to taking the emission spectra. The final solutions were 5 µM in both badan and BIR3, and approximately 20-30 µM in the test compound solutions. 50 µL of water were added to three of the wells by way of controls, to determine the intensity observed when the AVPC-badan was bound to BIR3. 190 µL of AVPC-badan and 1020 µL of buffer were mixed and added to three wells in 390 µL aliquots. 50 µL of water was added to these wells, again as controls, to determine the intensity of the unbound dye. Equilibrium constants were determined by relating the observed intensity of the test solution (as determined by the area under the emission curve) to the average values obtained from the control experiments.

Assay Results:

Assay results are reported relative to the $K_D$ found for AVPI, the tetrapeptide based on the sequence of the natural binding partner, in each assay. In this way, results were normalized for day to day variation. Results are reported as follows, as ratios of test compound $K_d$ to AVPI $K_3$: "--"=no binding observed at the concentration used in the assay; "NA"=Not assayed; ±=ratio greater than $10^{-4}$ (i.e., test compound bound with $K_D$ greater than $10^{-4}$ that of AVPI); +=ratio greater than $10^{-3}$; ++=ratio greater than $10^{-2}$; +++=ratio greater than $10^{-1}$.

Methylene bridged compounds:

| Number of Carbons (n) | KD (AVPI)/$K_D$(Homolog) | |
| --- | --- | --- |
| | without double bond | with doubble bond |
| 2 | ± | ± |
| 3 | -- | + |
| 4 | +++ | +++ |
| 5 | ++ | +++ |
| 6 | ± | NA |

Oxazole-Based Compounds:

| Homolog | Name | $K_D$(AVPI)/$K_D$(Homolog) |
| --- | --- | --- |
| | AoxSPF-OCH3 | ++ |
| | AoxSPF-OH | ++ |
| | AoxTPF-OCH3 | ++ |

-continued
| Homolog | Name | $K_D$(AVPI)/$K_D$(Homolog) |
|---|---|---|
| 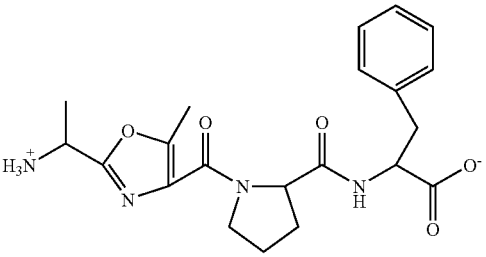 | AoxTPF-OH | +++ |
| 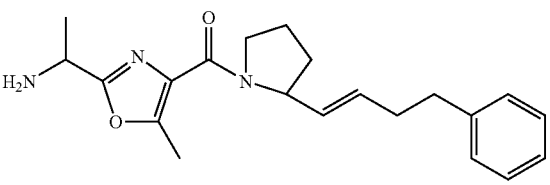 | AoxTPF-unsat | + |
| 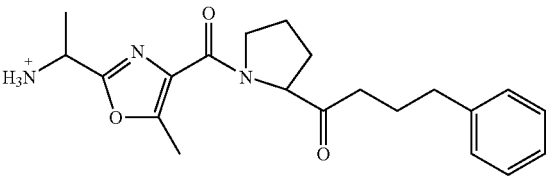 | AoxSPF-ketone | -- |
| 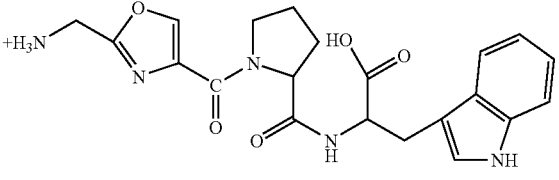 | AoxSPW | + |
| 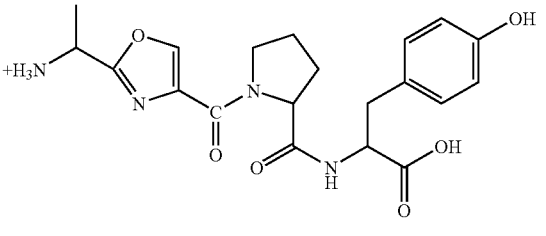 | AoxSPY | ++ |
| 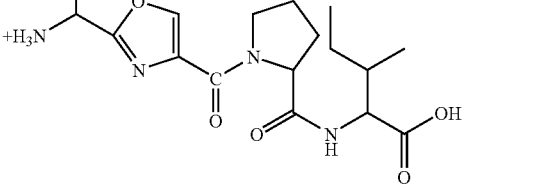 | AoxSPI | -- |

Phenylalanine Derivatives:
| Phenylalanine Derivative | Name | $K_D$(AVPI)/$K_D$(Homolog) | |
| --- | --- | --- | --- |
| | | Ala-Val-Pro-Phe Derivative | Ala-Arg-Pro-Phe Derivative |
| 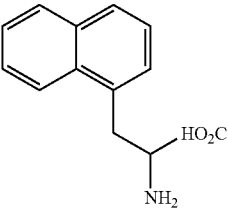 | 1-Naphthalene | +++ | NA |
| 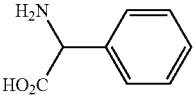 | Phenylglycine | +++ | +++ |
| 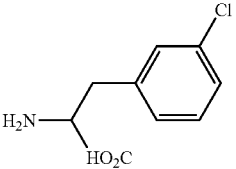 | 3-Chlorophenylalanine | +++ | +++ |
| 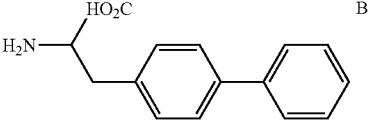 | Biphenylalanine | +++ | +++ |
| 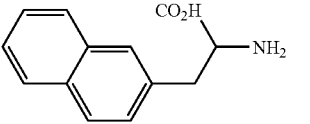 | 2-Naphthalene | +++ | NA |
| 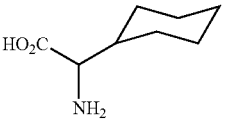 | Cyclohexylglycine | +++ | NA |
| 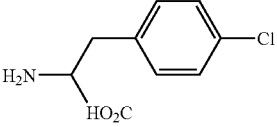 | 4-Chlorophenylalanine | +++ | +++ |
| 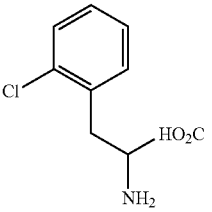 | 2-Chlorophenylalanine | +++ | +++ |

-continued

| Phenylalanine Derivative | Name | K_D(AVPI)/K_D(Homolog) | |
|---|---|---|---|
| | | Ala-Val-Pro-Phe Derivative | Ala-Arg-Pro-Phe Derivative |
| 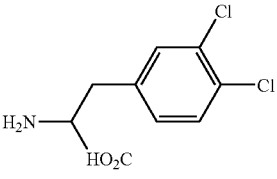 | 3,4-Dichlorophenylalanine | +++ | +++ |
| 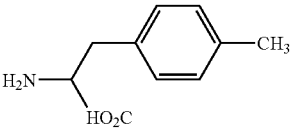 | 4-Methylphenylalanine | +++ | +++ |
| 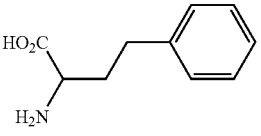 | Homophenylalanine | +++ | NA |
| 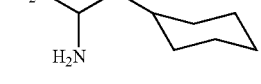 | Cyclohexylalanine | +++ | +++ |
| 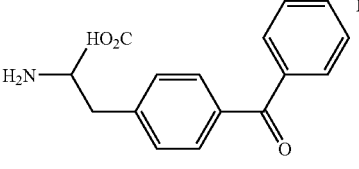 | Benzoylphenylalanine | +++ | +++ |
| 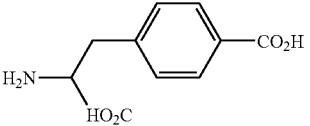 | 4-Carboxyphenylalanine | +++ | NA |

Proline Derivatives:

| Proline Derivative | Name | K_D(AVPI)/K_D(Homolog) |
|---|---|---|
| 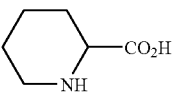 | Homoproline | +++ |
| 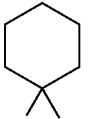 | 4-Hydroxyproline | +++ |

-continued

| Proline Derivative | Name | K_D(AVPI)/K_D(Homolog) |
|---|---|---|
| 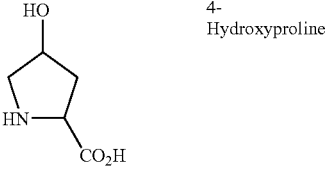 | 1-Amino-1-cyclohexane-carboxylic acid | ± |
|  | Cycloleucine | ± |

What is claimed:

1. A compound of formula I

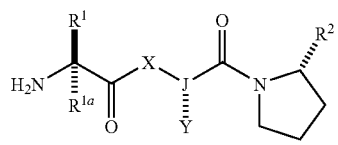

wherein
R$^1$ is methyl, ethyl, n-propyl, isopropyl, or ethenyl;
R$^{1a}$ is H or methyl;
X is —O—, —S—, CH$_2$—, or —NH—, and J is —CH— or —N—, provided that when J is —N—, X is —CH$_2$— or —NH—;
Y is H, methyl, ethyl, n-propyl, or isopropyl;
R$^2$ is:

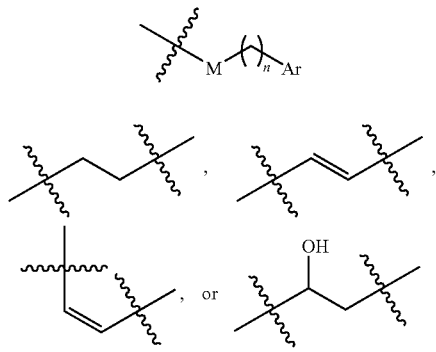

Ar is:

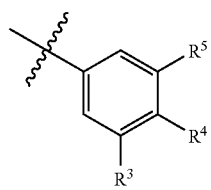

R$^3$, R$^4$ and R$^5$ are each independently H, methyl, ethyl, n-propyl, isopropyl, halo, cyano, —(CH$_2$)$_p$—C(=O)OH, —(CH$_2$)$_p$—C(=O)O-alkyl, or C(=O)NH$_2$;
n and p are each independently the integer 0, 1, 2, or 3, and the sum of n plus p is the integer 2 or 3;
provided that at least one of R$^3$, R$^4$ and R$^5$ is H, methyl, ethyl, n-propyl, isopropyl, halo or cyano;
provided that when one or more of R$^3$ and R$^5$ is isopropyl, R$^4$ is other than isopropyl;
provided that when R$^4$ is isopropyl, R$^3$ and R$^5$ are each independently other than isopropyl;
or a pharmaceutically acceptable salt thereof,
wherein said compound binds to an Inhibitor of Apoptosis Protein (IAP).

2. A compound according to claim 1, of formula I, wherein one of R$^3$, R$^4$, and R$^5$ is —(CH$_2$)$_p$—C(=O)OH, —CH$_2$)$_p$—C(=O)O-alkyl, —(CH$_2$)$_p$—C(=O)NH$_2$.

3. A compound according to claim 2, of formula I, wherein p is the integer 0.

4. A compound according to claim 2, of formula I, wherein one of R$^3$, R$^4$, and R$^5$ is —(CH$_2$)—C(=O)OH or —(CH$_2$)—C(=O)O-alkyl.

5. A compound according to claim 4, of formula I wherein p is the integer 0.

6. A compound according to claim 4, of formula I, wherein one of R$^3$, R$^4$, and R$^5$ is —(CH$_2$)—C(=O)OH.

7. A compound according to claim 6, of formula I wherein p is the integer 0.

8. A compound according to claim 1, of formula I wherein the sum of (n+p) is the integer 2.

9. A compound according to claim 1, of formula I, wherein M is:

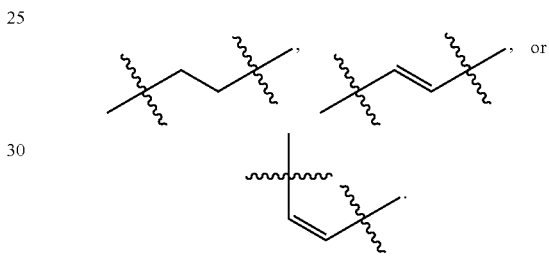

10. A compound according to claim 1, of formula I, wherein Ar is:

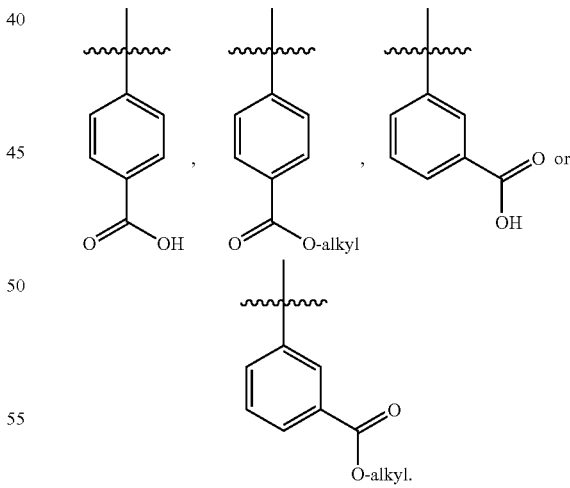

* * * * *